United States Patent
Dunham et al.

(10) Patent No.: US 12,285,260 B2
(45) Date of Patent: Apr. 29, 2025

(54) CATHETER-DEPLOYABLE SOFT ROBOTIC SENSOR ARRAYS AND PROCESSING OF FLEXIBLE CIRCUITS

(71) Applicant: Cornell University, Ithaca, NY (US)

(72) Inventors: Simon Dunham, New York, NY (US); Bobak Mosadegh, New York, NY (US); Varun Umesh Kashyap, New York, NY (US); Tejas Doshi, New York, NY (US); Alexandre Caprio, New York, NY (US)

(73) Assignee: Cornell University, Ithaca, NY (US)

( * ) Notice: Subject to any disclaimer, the term of this patent is extended or adjusted under 35 U.S.C. 154(b) by 106 days.

(21) Appl. No.: 17/920,638

(22) PCT Filed: Apr. 23, 2021

(86) PCT No.: PCT/US2021/028940
§ 371 (c)(1),
(2) Date: Oct. 21, 2022

(87) PCT Pub. No.: WO2021/217066
PCT Pub. Date: Oct. 28, 2021

(65) Prior Publication Data
US 2023/0146045 A1    May 11, 2023

Related U.S. Application Data

(60) Provisional application No. 63/015,344, filed on Apr. 24, 2020.

(51) Int. Cl.
*H05K 3/00*     (2006.01)
*A61B 5/00*     (2006.01)
(Continued)

(52) U.S. Cl.
CPC .............. *A61B 5/287* (2021.01); *A61B 5/283* (2021.01); *A61B 5/367* (2021.01); *A61B 5/6853* (2013.01);
(Continued)

(58) Field of Classification Search
CPC ....... H05K 1/0277; H05K 1/028; A61B 5/367
See application file for complete search history.

(56) References Cited

U.S. PATENT DOCUMENTS

| 5,345,936 A | 9/1994 | Pomeranz et al. |
| 5,904,680 A | 5/1999 | Kordis et al. |

(Continued)

FOREIGN PATENT DOCUMENTS

| KR | 101799179 B1 | 11/2017 |
| WO | WO-2006/074159 A2 | 7/2006 |

OTHER PUBLICATIONS

International Preliminary Report on Patentability on PCT PCT/US2020/059452 Dtd May 19, 2022.
(Continued)

*Primary Examiner* — Cachet I Proctor
(74) *Attorney, Agent, or Firm* — Foley & Lardner LLP

(57) ABSTRACT

Methods for fabricating flexible/stretchable circuits can include identifying one or more regions of a printed circuit board (PCB) for selectively removing insulation material. The PCB can include one or more electrically conductive structures arranged on an insulation layer. The method can include applying, within each region of the one or more regions, thermal energy via a heat source to a surface of the PCB within the region such that insulation material of the insulation layer is removed from the region while a portion of the insulation layer beneath the one or more electrically
(Continued)

conductive structures is maintained. The flexible/stretchable circuit can be laminated on a soft actuator to form a soft robotic device.

20 Claims, 29 Drawing Sheets

(51) Int. Cl.
    *A61B 5/28*         (2021.01)
    *A61B 5/283*       (2021.01)
    *A61B 5/287*       (2021.01)
    *A61B 5/367*       (2021.01)
    *H05K 1/02*        (2006.01)

(52) U.S. Cl.
    CPC ......... *A61B 5/6858* (2013.01); *H05K 3/0032* (2013.01); *H05K 3/0064* (2013.01); *A61B 2562/166* (2013.01); *H05K 1/0277* (2013.01); *H05K 2201/09263* (2013.01); *H05K 2203/107* (2013.01)

(56) References Cited

U.S. PATENT DOCUMENTS

| | | | |
|---|---|---|---|
| 6,115,626 | A | 9/2000 | Whayne et al. |
| 9,545,216 | B2* | 1/2017 | D'Angelo ............... A61B 18/24 |
| 9,757,050 | B2* | 9/2017 | Ghaffari .................. A61B 5/05 |
| 10,955,671 | B2* | 3/2021 | Haba ........................ G06F 3/147 |
| 11,559,225 | B1 | 1/2023 | Lee et al. |
| 11,642,064 | B2 | 5/2023 | Sterrett et al. |
| 11,878,095 | B2 | 1/2024 | Beeckler et al. |
| 2003/0086206 | A1* | 5/2003 | Kube ...................... G11B 5/4833 |
| 2004/0167509 | A1 | 8/2004 | Taimisto |
| 2006/0211191 | A1* | 9/2006 | Sabev .................... H05K 1/167 438/238 |
| 2008/0004679 | A1 | 1/2008 | Naghavi et al. |
| 2008/0140072 | A1 | 6/2008 | Stangenes et al. |
| 2008/0314867 | A1 | 12/2008 | Woychik et al. |
| 2009/0203962 | A1 | 8/2009 | Miller et al. |
| 2010/0155109 | A1* | 6/2010 | Takahashi ............... H05K 1/028 29/830 |
| 2010/0204560 | A1* | 8/2010 | Salahieh .................. A61B 5/01 606/41 |
| 2011/0232948 | A1* | 9/2011 | Sato ......................... H05K 3/42 174/262 |
| 2011/0274829 | A1* | 11/2011 | Feurer ............... H01L 23/49822 427/97.6 |
| 2012/0126460 | A1 | 5/2012 | Shin et al. |
| 2013/0267081 | A1 | 10/2013 | Fox et al. |
| 2014/0268780 | A1 | 9/2014 | Wang et al. |
| 2015/0177886 | A1 | 6/2015 | Gorsica et al. |
| 2015/0351652 | A1* | 12/2015 | Marecki ............. A61B 18/1492 29/829 |
| 2015/0366508 | A1* | 12/2015 | Chou ..................... A61N 1/056 600/467 |
| 2015/0373831 | A1 | 12/2015 | Rogers et al. |
| 2016/0037624 | A1 | 2/2016 | Yu et al. |
| 2016/0165719 | A1* | 6/2016 | Li .......................... H05K 1/148 361/749 |
| 2016/0183363 | A1 | 6/2016 | Lee et al. |
| 2016/0353978 | A1 | 12/2016 | Miller et al. |
| 2017/0040306 | A1 | 2/2017 | Kim et al. |
| 2017/0136496 | A1 | 5/2017 | Jacobs et al. |
| 2017/0333124 | A1 | 11/2017 | Gelbart et al. |
| 2018/0067003 | A1 | 3/2018 | Michiwaki |
| 2018/0068759 | A1 | 3/2018 | Bihler et al. |
| 2018/0184982 | A1 | 7/2018 | Basu et al. |
| 2018/0192520 | A1* | 7/2018 | Choong ................. H05K 1/189 |
| 2018/0200524 | A1 | 7/2018 | Toth et al. |
| 2018/0236220 | A1 | 8/2018 | Glenn et al. |
| 2018/0343741 | A1 | 11/2018 | Williams et al. |
| 2019/0030710 | A1* | 1/2019 | Lessing .................... B25J 15/12 |
| 2022/0387675 | A1* | 12/2022 | Farokhnia ............... A61L 29/16 |

OTHER PUBLICATIONS

International Search Report and Written Opinion on PCT PCT/US2020/059452 Dtd Mar. 23, 2021.
International Search Report and Written Opinion on PCT PCT/US2021/028940 Dtd Oct. 22, 2021.
Lin et al. "Design and fabrication of stretchable multilayer self-aligned interconnects for flexible electronics and large-area sensor arrays using excimer laser photoablation" IEEE Electron Device Letters, vol. 30, No. 1, Jan. 2009, retrieved from <https://ieeexplore.ieee.org/abstract/document/4703248>.
International Preliminary Report on Patentability for PCT/US2021/028940 dated Nov. 3, 2022.
Foreign Search Report on EP Dtd Oct. 18, 2023.
Extended European Search Report for EP Application No. 21791942.2, dated May 29, 2024, 9 pgs.

* cited by examiner

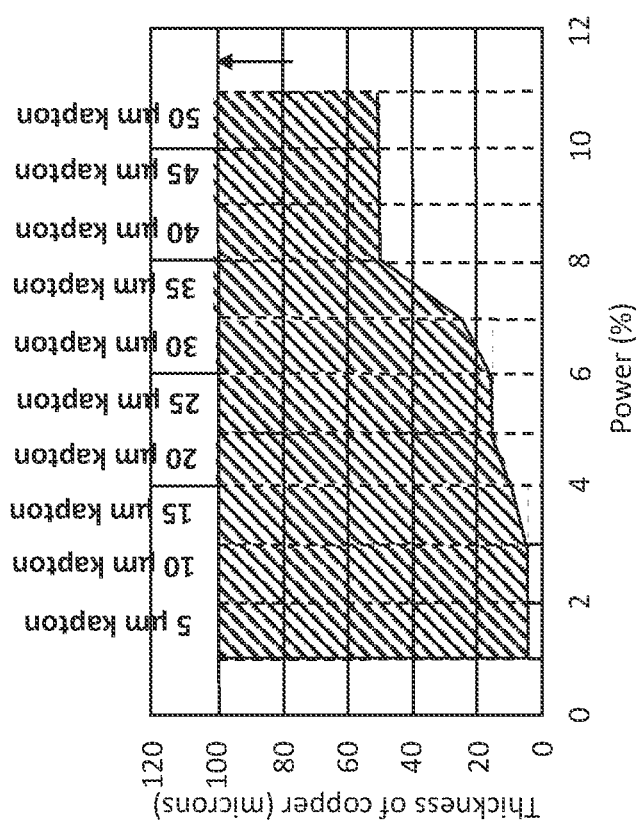

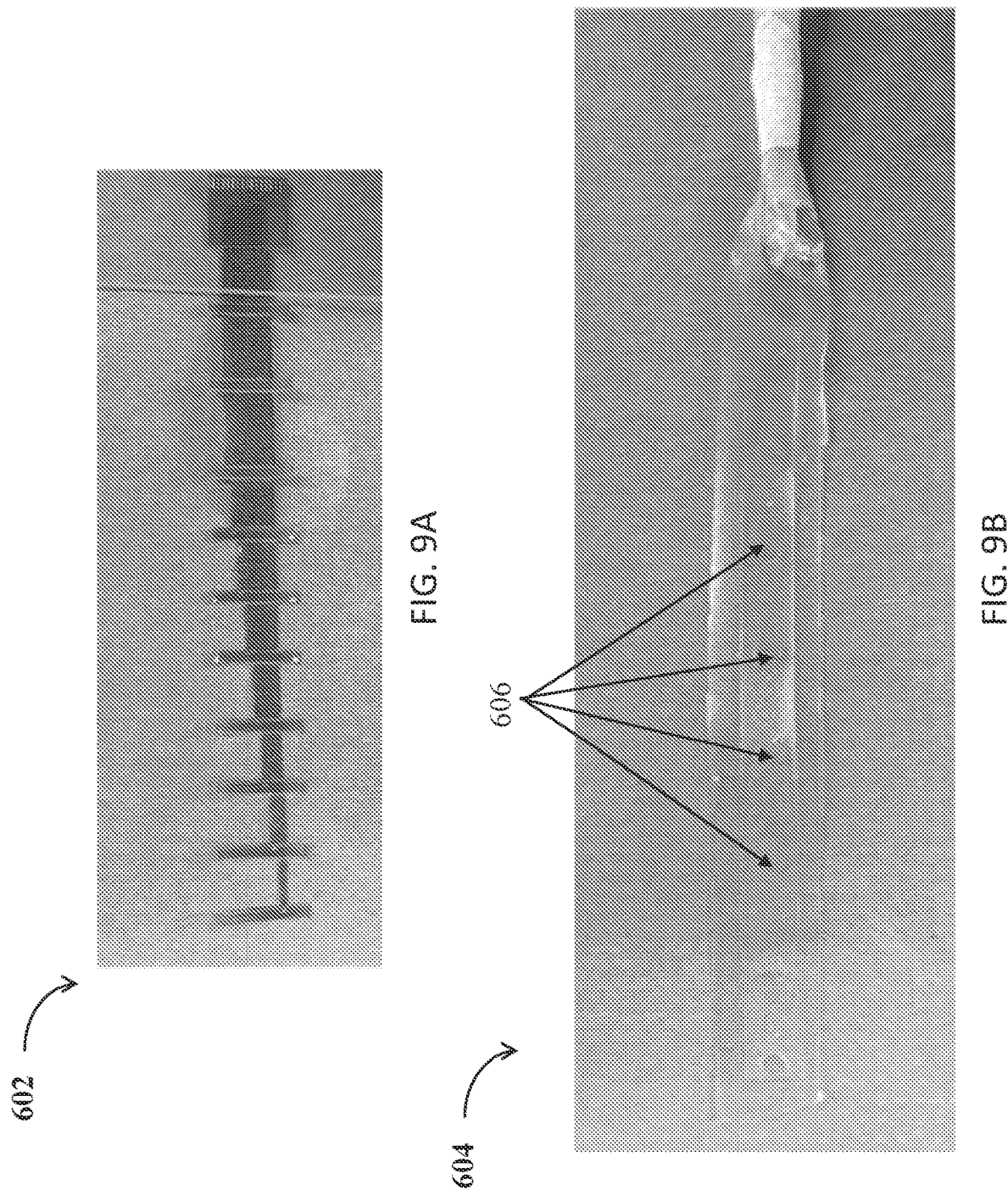

CATHETER-DEPLOYABLE SOFT ROBOTIC SENSOR ARRAYS AND PROCESSING OF FLEXIBLE CIRCUITS

CROSS-REFERENCES TO RELATED APPLICATIONS

This application is a U.S. National Phase Application under 35 U.S.C. § 371 of International Application No. PCT/US2021/028940, filed on Apr. 23, 2021, and claims the benefit of and priority to U.S. Provisional Patent Application No. 63/015,344, entitled "CATHETER-DEPLOYABLE SOFT ROBOTIC SENSOR ARRAYS AND PROCESSING OF FLEXIBLE CIRCUITS," filed Apr. 24, 2020, the contents of each of which are hereby incorporated by reference in their entireties.

STATEMENT REGARDING FEDERALLY SPONSORED RESEARCH

This invention was made with government support under contract no. W81XWH-18-1-0201 awarded by the Department of Defense. The government has certain rights in the invention.

BACKGROUND

Atrial fibrillation (AFib) is the most common form of cardiac arrhythmia, with a worldwide prevalence of more than 33 million people worldwide. AFib causes an irregular and often rapid heart rate that may cause symptoms like palpitations, fatigue, and shortness of breath. It originates from the interplay between genetic predisposition, ectopic electrical activity, and abnormal atrial tissue substrate. AFib can affect the efficiency of cardiac output and promote the formation of blood clots inside the left atrium (particularly the left atrial appendage). If these clots embolize and travel from the heart to the brain, they could result in a stroke. AFib is associated with a 1.5- to 2-fold increase in death and heart failure and about 3- to 5-fold higher risk of stroke. Furthermore, AFib is also associated with a greater risk of hospitalization, with 10 to 40% of patients with this disease hospitalized annually.

Radiofrequency catheter ablation has emerged as an established and widespread technique for the treatment of AFib via a minimally invasive catheter procedure. Cardiac electrograms can be mapped using a sensing catheter, and then radiofrequency energy is applied to the heart muscle at particular locations to cauterize the circuits that trigger AFib, using an ablation catheter. This procedure can provide rhythm control in patients with paroxysmal and persistent AFib. There is strong evidence that AFib ablation therapy improves quality of life, reduces health resource utilization, and improves heart function in patients with heart failure. For the ablation procedure, electro-anatomical mapping techniques have been developed to guide the procedure. By recording the electrical activity inside the heart, the circuits that are generating AFib can be identified.

Cardiac mapping and ablation helps provide an effective means of treatment for Atrial fibrillation (AFib). Accurate and efficient cardiac mapping and ablation calls for medical devices capable of conforming to the internal structure of the heart chamber of interest. Manufacturing such devices that can also be deployed to the heart chamber of interest poses various technical challenges.

SUMMARY

In various potential embodiments, the systems, devices and methods described in this disclosure relate to fabrication of durable soft robotic devices and fabrication of flexible circuits as well as implementations of such robotic devices and flexible circuits. The soft robotic devices described herein are suitable for efficient left atrial mapping as well as other applications, and are catheter deployable. Once deployed, the soft robotic device can be actuated to expand and conform to the internal structure of an organ of interest. Conforming to the internal structure of the organ of interest or other anatomical structures allows for more precise mapping or sensing of signals generated by the organ. Different geometric configurations can be provided for different anatomical configurations. The fabrication of flexible circuits can involve using scalable circuits, e.g., printed circuit boards (PCBs), and applying selective removal of insulation layers while retaining the integrity of the circuit. The flexible circuit can be fixated or laminated on an outer surface of a soft actuator to form the soft robotic device.

At least one aspect of the present disclosure is directed to a method. The method can include identifying one or more regions of a printed circuit board (PCB) for selectively removing insulation material. The PCB can include one or more electrically conductive structures arranged on an insulation layer. The method can include applying, within each region of the one or more regions, thermal energy via a heat source to a surface of the PCB within the region such that insulation material of the insulation layer is removed from the region while a portion of the insulation layer beneath the one or more electrically conductive structures is maintained.

In some implementations, applying the thermal energy can include applying the thermal energy along a raster path within the region. In some implementations, the method can further include determining an output thermal energy range of the heat source to cause the insulation material of the insulation layer to be removed from the region while maintaining the portion of the insulation layer beneath the one or more electrically conductive structures, and setting the heat source to generate the thermal energy according to the output thermal energy range prior to applying the thermal energy to the surface of the PCB. In some implementations, the output thermal energy range is determined based on a first temperature specific to the insulation layer and a second temperature specific to the one or more electrically conductive structures. In some implementations, the output thermal energy range can be based on a thickness of the insulation layer. In some implementations, the output thermal energy range can be based on a thickness of the one or more electrically conductive structures.

In some implementations, the heat source can be a laser cutter and applying the thermal energy to the surface of the PCB can include applying a laser beam of the laser cutter to the surface of the PCB according to a raster path within the region. In some implementations, the method can further include determining an output power range of the laser cutter to cause the insulation material of the insulation layer to be removed while maintaining the portion of the insulation layer beneath the one or more electrically conductive structures, and setting the laser cutter according to the output power range prior to applying the laser beam to the surface of the PCB.

In some implementations, the PCB can include one or more sensors and identifying one or more regions can include identifying one or more first regions of the PCB that do not include any of the one or more sensors. The one or more sensors can be located within one or more second regions of the PCB where the insulation layer is not removed. In some implementations, the one or more sensors can include a plurality of sensors, and the one or more second regions include a plurality of second regions. The plurality of sensors can be distributed among the plurality of second regions.

In some implementations, the one or more electrically conductive structures can include copper traces. In some implementations, the insulation layer can include a polymer layer. In some implementations, the one or more electrically conductive structures can be exposed within the one or more regions to sense electrical voltage of a surrounding environment. In some implementations, the one or more electrically conductive structures can have a serpentine shape to allow the one or more electrically conductive structures to stretch within the one or more regions when the insulation layer is removed. In some implementations, the maintained portion of the insulation layer beneath the one or more electrically conductive structures can allow the one or more electrically conductive structures to maintain mechanical integrity within the region. In some implementations, the PCB can include a flexible PCB.

In some implementations, the PCB can include a plurality of insulation layers. The thermal energy can be applied, within each region of the one or more regions, to the surface of the PCB, such that insulation material of the plurality of insulation layers is removed from the region while a portion of one or more insulation layers beneath the one or more electrically conductive structures is maintained.

At least one other aspect of the present disclosure is directed to an apparatus. The apparatus can include a plurality of blocks of an insulation layer including a one or more circuit components. Each block connected to an adjacent block via one or more connectors made from the insulation layer. The apparatus can include one or more electrically conductive structures deposited on and defining a first surface of the one or more connectors. The one or more electrically conductive structures extending between and across the plurality of blocks.

In some implementations, the one or more circuit components can include one or more sensors distributed among the plurality of blocks of the insulation layer. In some implementations, the one or more electrically conductive structures can include copper traces. In some implementations, the insulation layer includes a polymer layer. In some implementations, a portion of the one or more electrically conductive structures extending between the plurality of blocks can be exposed to sense electrical voltage of a surrounding environment.

In some implementations, a thickness of the plurality of blocks is about about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm or about 140 µm. In some implementations, a thickness of the one or more connectors can be about 15 µm, about 20 µm, about 25 µm, about 30 µm, about 35 µm, about 40 µm, about 45 µm, about 50 µm, about 55 µm, about 60 µm, about 65 µm, about 70 µm or about 75 µm. In some implementations, a thickness of the one or more electrically conductive structures is about 15 µm, about 20 µm, about 25 µm, about 30 µm, about 35 µm, about 40 µm, about 45 µm, about 50 µm, about 55 µm, about 60 µm, about 65 µm, about 70 µm or about 75 µm.

At least one other aspect of the present disclosure is directed to a method. The method can include aligning at least one flexible circuit with a soft actuator. Each flexible circuit of the at least one flexible circuits can include a plurality of blocks of an insulation layer including a one or more circuit components, and one or more electrically conductive structures deposited on and defining a first surface of the one or more connectors. Each block can be connected to an adjacent block via one or more connectors made from the insulation layer. The one or more electrically conductive structures can extend between and across the plurality of blocks. The method can include laminating the at least one flexible circuit with a polymer sheet on a surface of the soft actuator to form a soft robotic device. The polymer sheet can be configured to provide, for the at least one flexible circuit, insulation and mechanical fixation to the soft actuator.

In some implementations, the soft actuator can include a plurality of beams and the method can include aligning each flexible circuit of a plurality of flexible circuits to a corresponding beam of the plurality of beams, and laminating each flexible circuit with a separate polymer sheet on a surface of the corresponding beam of the soft actuator. In some implementations, the soft robotic device can be a cardiac mapping device deployable into a heart chamber using a catheter. In some implementations, the polymer sheet can be a polyurethane sheet. In some implementations, the soft actuator can include nitinol.

In some implementations, the soft actuator can include polymer and the method can further include manufacturing the soft actuator. Manufacturing the soft actuator can include arranging a sheet of water soluble polymer between two layers of polymer, and thermally bonding the two layers of polymer around respective borders. The sheet of water soluble polymer can act as a sacrificial layer to form an inflatable closed channel between the two bonded layers of polymer. In some implementations, the method can further include making a plurality of cutouts in the sheet of water soluble polymer, and thermally bonding the two layers of polymer at the plurality of cutouts to achieve bending regions in the soft actuator when the soft actuator is actuated. The plurality of cutouts can be distributed along a length of the sheet of water soluble polymer. In some implementations, the water soluble polymer can include polyvinyl alcohol.

In some implementations, the method can further include making one or more cutouts in the polymer sheet. The one or more cutouts partially exposing portions of the one or more electrically conductive structures extending between the plurality of blocks of the insulation layer. In some implementations, the one or more electrically conductive structures and the one or more connectors can have serpentine shapes. In some implementations, one or more electrically conductive structures can include copper traces. In some implementations, each connector of the one or more connectors can be substantially aligned with the conductive structure deposited on the connector At least one other aspect of the present disclosure is directed to apparatus. The apparatus can include an inflatable actuator and one or more flexible circuits laminated with one or more polymer sheets on a surface of the inflatable actuator. Each flexible circuit can include a plurality of blocks of an insulation layer including a one or more circuit components, where each block is connected to an adjacent block via one or more connectors made from the insulation layer, and one or more electrically conductive structures deposited on and defining a first surface of the one or more connectors, the one or more electrically conductive structures extending between and across the plurality of blocks.

In some implementations, each connector of the one or more connectors can be substantially aligned with a corresponding conductive structure deposited on the connector. In some implementations, the apparatus can be a cardiac mapping device deployable into a heart chamber using a catheter. In some implementations, the inflatable actuator can include nitinol. In some implementations, the inflatable actuator can include polymer.

In some implementations, the inflatable actuator can include a sheet of water soluble polymer arranged between two layers of polymer. The two layers of polymer can be thermally bonded around respective borders and the sheet of water soluble polymer can act as a sacrificial layer to form an inflatable closed channel between the two bonded layers of polymer. In some implementations, the water soluble polymer can include polyvinyl alcohol. In some implementations, the sheet of water soluble polymer can include a plurality of cutouts distributed along a length of the sheet of water soluble polymer. The two layers of polymer can be thermally bonded at the plurality of cutouts to achieve bending regions in the inflatable actuator.

In some implementations, the one or more polymer sheets can include one or more cutouts exposing portions of the one or more electrically conductive structures extending between the plurality of blocks of the insulation layer. In some implementations, the one or more electrically conductive structures can include copper traces deposited on the one or more connectors.

At least one other aspect of the present disclosure is directed to a method for manufacturing flexible sensor arrays. The method can include identifying one or more regions of a flexible printed circuit board (PCB) for selectively removing polymer. The flexible PCB can include one or more sensors and one or more electrically conductive serpentine structures between a first polymer layer and a second polymer layer. Each electrically conductive serpentine structure can be connected to a corresponding sensor of the one or more sensors. The method can include applying, within each region of the one or more regions, thermal energy via a heat source to a first surface of the flexible PCB along a raster path within the region such that polymer in the first polymer layer and the second polymer layer is removed from the region while a portion of the second polymer layer beneath the one or more electrically conductive serpentine structures is maintained.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form. For example, by appropriate computer programs, which can be carried on appropriate carrier media (computer readable media), which can be tangible carrier media (e.g. disks) or intangible carrier media (e.g. communications signals). Aspects can also be implemented using suitable apparatus, which can take the form of programmable computers running computer programs arranged to implement the aspect. As used in the specification and in the claims, the singular form of 'a', 'an', and 'the' include plural referents unless the context clearly dictates otherwise.

BRIEF DESCRIPTION OF THE DRAWINGS

The accompanying drawings are not intended to be drawn to scale, unless specifically indicated in a particular drawing. Like reference numbers and designations in the various drawings indicate like elements. For purposes of clarity, not every component can be labeled in every drawing. In the drawings:

FIGS. 5A-5D depict experimental and simulation results illustrating heat masking and processing windows to achieve successful self-aligned removal, according to example embodiments of the current disclosure;

FIGS. 9A-9H show diagrams illustrating various steps a process of manufacturing a stretchable/flexible soft robotic device, according to example embodiments of the current disclosure;

DETAILED DESCRIPTION

Figure 1:
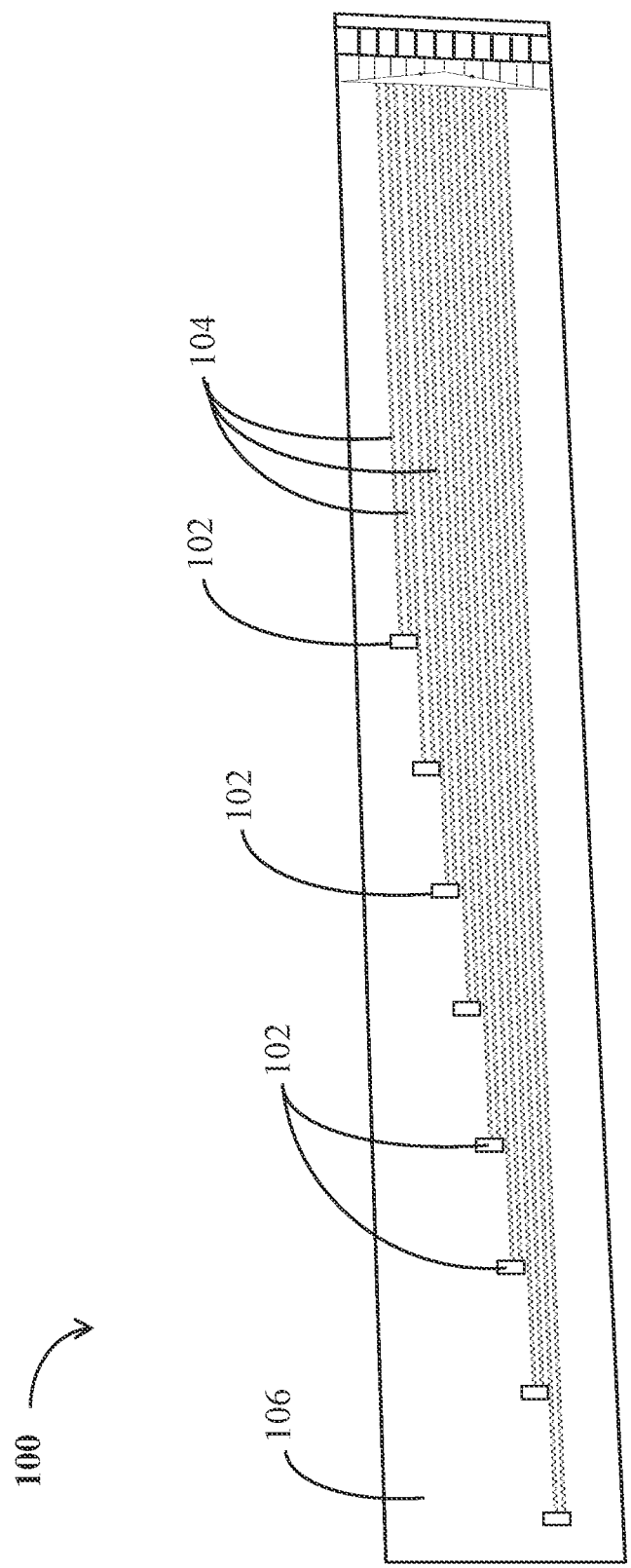
FIG. 1 depicts an example PCB, according to example embodiments of the current disclosure.

Devices or systems that perform cardiac mapping and ablation to treat AFib can provide an effective means of treatment. Existing cardiac mapping devices, however, have limitations that either require tedious point-by-point mapping of a cardiac chamber or have limited ability to conform to the complex anatomy of a patient's cardiac chamber. For instance, some electro-anatomical mapping systems have limited spatiotemporal resolution for detecting localized AFib drivers because of their sequential spatiotemporal characteristics, intermittent firing, and complex atrial anatomy. These are some of the reasons for suboptimal outcomes after ablation in some forms of AFib. Subsequently developed advanced mapping catheters, such as basket catheters, with multi-electrode arrays mitigate this drawback. The advantages of multi-electrode mapping include quicker voltage mapping and more accurate assessment of activation sequence. However, conventional multi-electrode catheter designs are fabricated from sensor arrays that are deployed on a cage of inelastic materials (either metal wire or narrow strips of inelastic polymer film) designed to passively engage with tissue. These designs have limited conformability and other non-ideal mechanical response, such as spline bunching (e.g., a non-uniform distribution of the sensor arrays due to improper deployment/expansion of the device in the left atrium). The effective result of these unintended mechanical responses is that less than 50% of the sensors provide meaningful data.

In this disclosure, implementations of soft robotic devices, e.g., multi-electrode soft robotic sensor array (SRSA) devices, and methods for developing such soft robotic devices are described. The soft robotic device can be equipped with a flexible, and/or stretchable, circuit such as an array of flexible/stretchable electronic sensors for voltage mapping. The form factor of the soft robotic device can be intended to match that of an entire cardiac chamber (e.g., left atrium) or other anatomical chamber, and can have a hydraulically actuated soft structure whose profile can facilitate deployment from a 13.5-Fr catheter. For instance, the SRSA device can uniformly conform at least 128 flexible sensors to the cardiac chamber (e.g., left atrium) tissue by hydraulically actuating a thin-walled polymer cage. In experimental testing, manufactured SRSA devices were deployed in four soft three-dimensional printed atrial models, and experimental testing results show that an average of about 85 to 90% of the sensors made tissue contact or were close enough (e.g., less than 2 mm distance, as assessed by micro-computed tomography (µ-CT)) to a left atrium inner wall to establish robust near-field sensing. Furthermore, the robustness of various designs were experimentally illustrated by deploying the devices from a 13.5-Fr catheter tube, and showing that sensors could undergo 100 cycles of actuation without reduction of performance.

The development of the soft robotic devices poses several challenges, such as scalable fabrication, integration and associated mechanical durability. To achieve conformable soft robotic devices, approaches for fabricating soft actuator designs with high degrees of complexity are used. The focus was on designs with the ability to conform to patient atria, or more generally to a complex chamber. Also, an approach for post-processing PCBs (e.g., flexible PCBs (flex-PCBs)) with electrically conductive structures (e.g., serpentine sensor array designs) can be used to fabricate stretchable and/or flexible circuits (e.g., flexible/stretchable sensor arrays). Specifically, a self-aligned post-processing method can be used to remove inelastic substrates (or insulation layers) of the flexible PCB (flex-PCB), and therefore increase the flexibility of the circuit or sensor array. The resulting flexible circuit (e.g., sensor array) can then be integrated or fixated on a soft actuator. Approaches for soft actuator fabrication are employed to develop complex geometry SRSAs capable of mounting at least 128 sensors, or other complex geometry circuits.

The processes and techniques described herein allow for fabrication of soft robotic devices without costly and time-consuming clean-room fabrication, using scalable PCB or flex-PCB manufacturing. The principles, procedures, and techniques described herein are valuable tools not only for cardiac mapping, but also for a wide variety of applications where sensor arrays or electric circuits are integrated on soft actuators, especially when thin or low-profile designs are needed. Embodiments of the systems and methods described in this disclosure are suitable for conformable medical devices that leverage the characteristics of stretchable electronics and soft robotics.

The remainder of the description is organized into multiple sections. For the purposes of reading the remainder description of the various implementations and techniques described herein, the following brief descriptions of the sections of the Specification may be helpful.

Section A describes flexible circuits and respective manufacturing processes.

Section B describes soft robotic devices and respective manufacturing processes.

A. Flexible Circuits and Respective Manufacturing Processes

Referring to FIG. 1, a PCB 100 is shown, according to example embodiments of the current disclosure. The PCB 100 can include one or more circuit components 102 and one or more electrically conductive structures 104. The one or more circuit components 102 and the one or more electrically conductive structures 104 can be arranged on an insulation layer 106 (also referred to as an insulation substrate).

In some implementations, the PCB 100 can be a flexible PCB where the insulation layer 106 can be, or can include, a polymer (or polyimide) layer. In some implementations, the PCB 100 can include a plurality of insulation layers 106. The plurality of insulation layers 106 can include, or can be, polymer layers. In such implementations, the circuit components 102 and/or the electrically conductive structures 104 can be arranged or sandwiched between two insulation layers (or polymer layers) of the plurality of insulation layers 106.

While FIG. 1 shows a plurality of circuit components 102 and a plurality of electrically conductive structures 104, the PCB can include any number of (e.g., one or more) circuit components 102 and any number of (e.g., one or more) electrically conductive structures 104. In some implementations, the circuit components 102 can include one or more sensors. The one or more sensors can include an electric voltage sensor, an electric impedance/resistance sensors, a force sensor, a shear sensor, an ultrasound senor, a thermal sensor, a position sensor, an electrocardiogram sensor, an electrochemical sensor or a combination thereof, among others.

In some implementations, each electrically conductive structure 104 can have a serpentine or flexuous shape that is bending or winding alternately from side to side. The electrically conductive structures 104 can also be referred to as metallic structures 104. The serpentine or flexuous shape can allow the electrically conductive structures 104 to stretch longitudinally, e.g., if not sealed to, or integrated on, the insulation layer 106. The electrically conductive structure(s) 104 can be electrically connected to the circuit component(s) 12 or sensor(s) a corresponding sensor 102. In some implementations, each electrically conductive structure 104 can be connected to a corresponding sensor. When in contact with, or in proximity to, organ tissue, the electrically conductive structure 104 can carry electric signals between the tissue to the corresponding sensor. The electrically conductive structures 104 can include (or can be) metallic traces, such as copper traces or traces of other conductive metals. The electrically conductive structures 104 can be relatively narrow (in width), e.g., acting as electric wires or electric connections.

Figure 2:
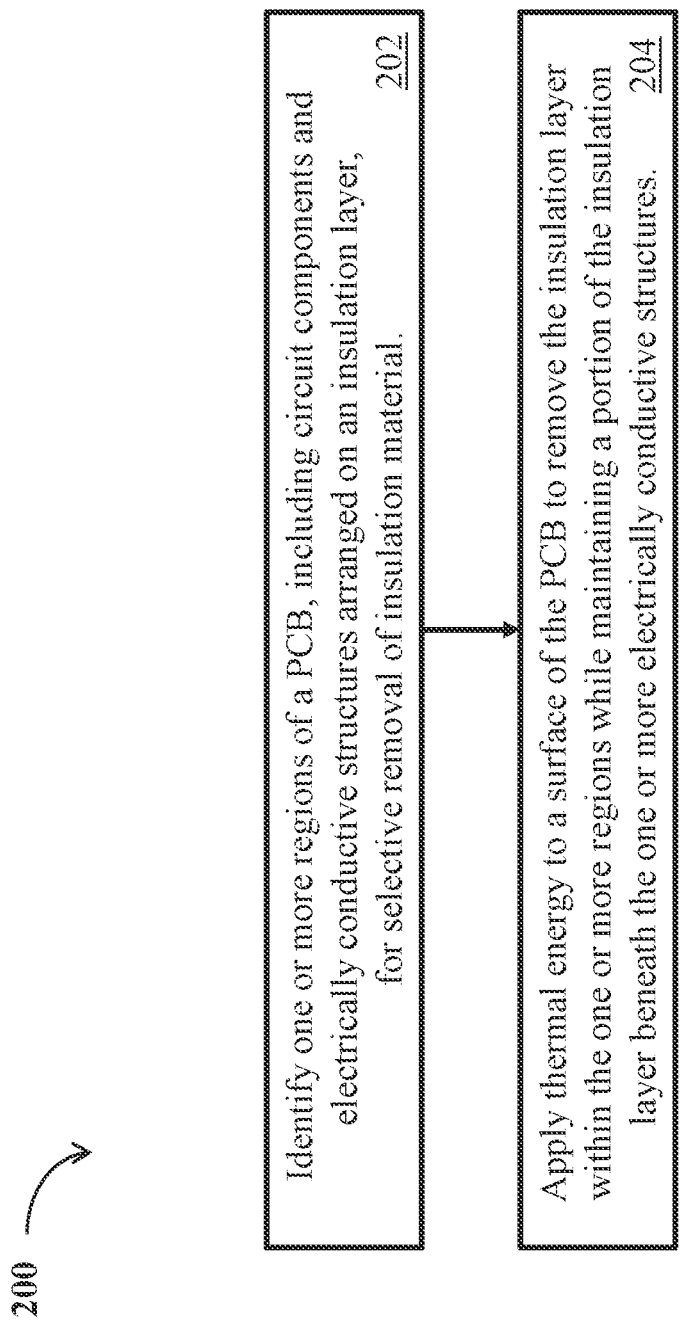
FIG. 2 depicts a flowchart illustrating a method of manufacturing flexible circuits, according to example embodiments of the current disclosure.

Referring now to FIG. 2, a flowchart illustrating a method 200 of manufacturing flexible circuits is shown, according to example embodiments of the current disclosure. The method 200 can include identifying one or more regions of a PCB for selective removal or of insulation material (STEP 202). The PCB can include one or more circuit components and one or more electrically conductive structures arranged on an insulation layer. The method 200 can include applying thermal energy to a surface of the flexible PCB to remove the insulation layer within the one or more regions while maintaining a portion of the insulation layer beneath the one or more electrically conductive structures (STEP 204).

Referring to FIGS. 1 and 2, the method 200 can include identifying one or more regions of PCB 100 for selectively removing insulation material (STEP 202). The PCB 100 can be as described above with regard to FIG. 1. For instance, PCB 100 can include or can be a flexible PCB and/or may include a plurality of insulation layers. In some implementations, identifying the one or more regions can include identifying one or more first regions of the PCB that do not include any of the circuit components 102, or do not include any of the sensors. For instance, the one or more regions can include the electrically conductive structure(s) 104, but not any of the circuit component(s) or not any of the sensors. The one or more regions can be window regions. For instance, each of the one or more regions can be a rectangular (or other shaped) region extending entirely along one dimension of the PCB 100. If a plurality of regions are defined, the regions can be non-overlapping. The regions may be parallel to one another.

The method 200 can include applying, within each region of the one or more regions, thermal energy via a heat source to a surface of the PCB within the region, such that insulation material of the insulation layer is removed from the region while a portion of the insulation layer beneath the one or more electrically conductive structures is maintained (STEP 204). The applied thermal energy can cause the insulation material of the insulation layer (or of the plurality of insulation layers) within the one or more regions to be removed, except the portion of the insulation material that is beneath the one or more electrically conductive structures within the one or more regions. The portion of the insulation material that is maintained can be viewed as an extension, within the one or more regions, to the one or more electrically conductive structures along a depth direction (e.g., a direction perpendicular to the surface of the PCB 100 which the heat is applied) of the PCB 100 or a depth direction of the one or more one or more electrically conductive structures. The portion of the insulation material that is maintained can be directly beneath the one or more electrically conductive structures, e.g., sealed to (or in contact with) a side of the one or more electrically conductive structures that is opposite to the surface of the PCB 100 to which the thermal energy is applied.

In some implementations, applying the thermal energy can include applying the thermal energy along a raster path within each region of the one or more regions. For instance, the heat source can be a laser cutter and applying the thermal energy to the surface of the PCB can include applying a laser beam of the laser cutter to the surface of the PCB according to a raster path within each region of the one or more regions.

Figure 3A:
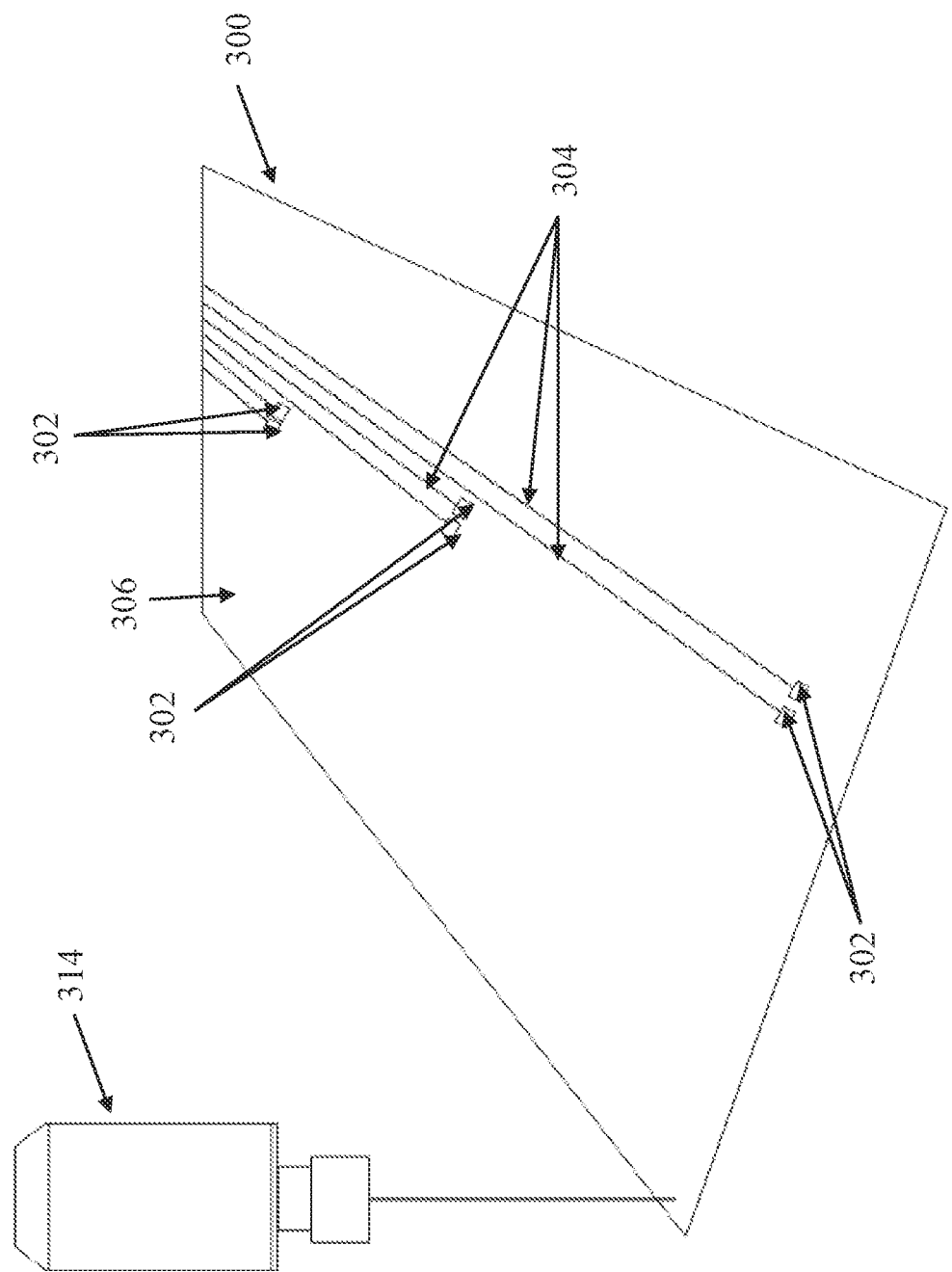
FIGS. 3A-3G depict a selective material removal process and related experimental results, according to example embodiments of the current disclosure.

Referring now to FIGS. 3A-3G, diagrams and images illustrating post-processing of electronics or PCBs to remove insulation layers within predefined regions and the effect of such post-processing, according to example embodiments of the current disclosure. FIG. 3A shows a flexible PCB 300 including circuit components 302 and electrically conductive structures 304 integrated on a polymer layer 306, and a laser cutter 314 for applying thermal energy to a surface of the PCB 300, e.g., top surface of PCB 300 in FIG. 3A. The electrically conductive structures 304 have serpentine or flexuous shapes, e.g., that are bending or winding alternately from side to side. The electrically conductive structures 304 are copper traces. In some implementations, the electrically conductive structures 304 can include other metallic traces. The electrically conductive structures 304 can as act electric wires or connections.

Figure 3B:
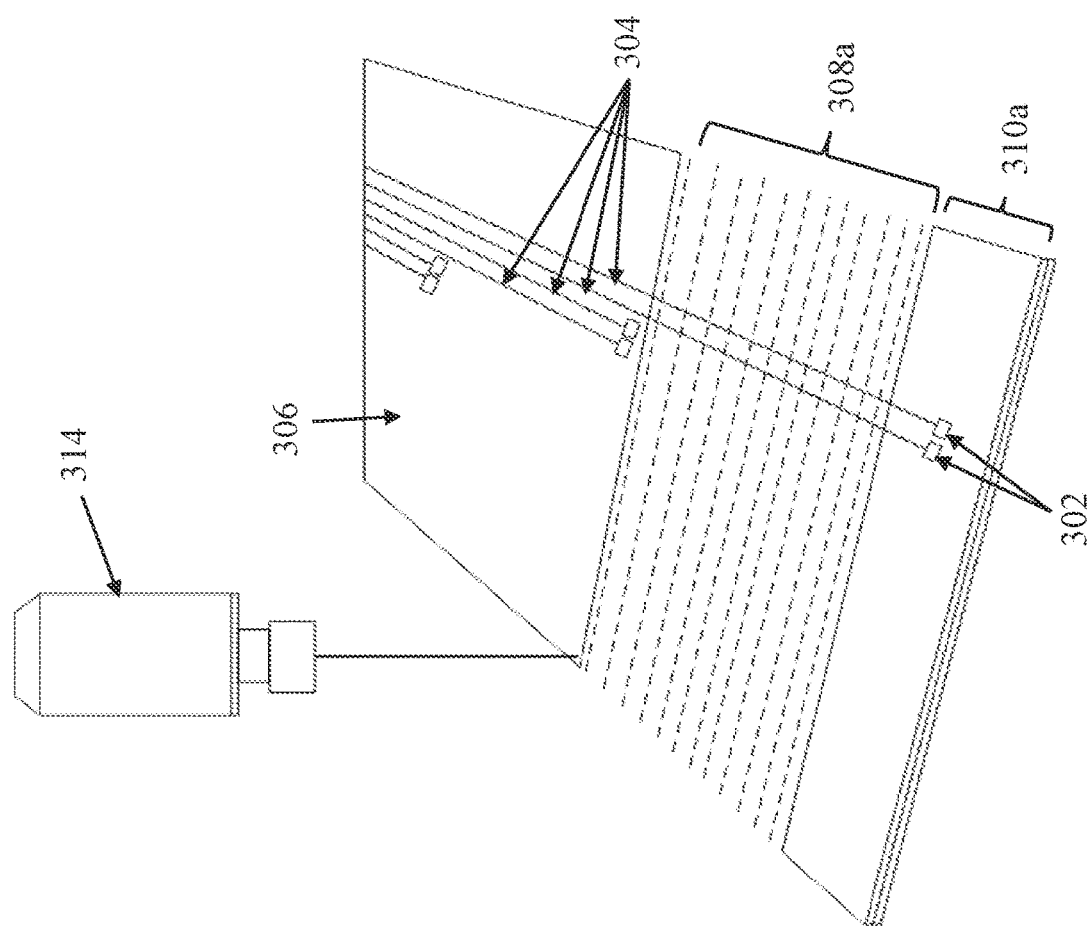
Figure 3C:
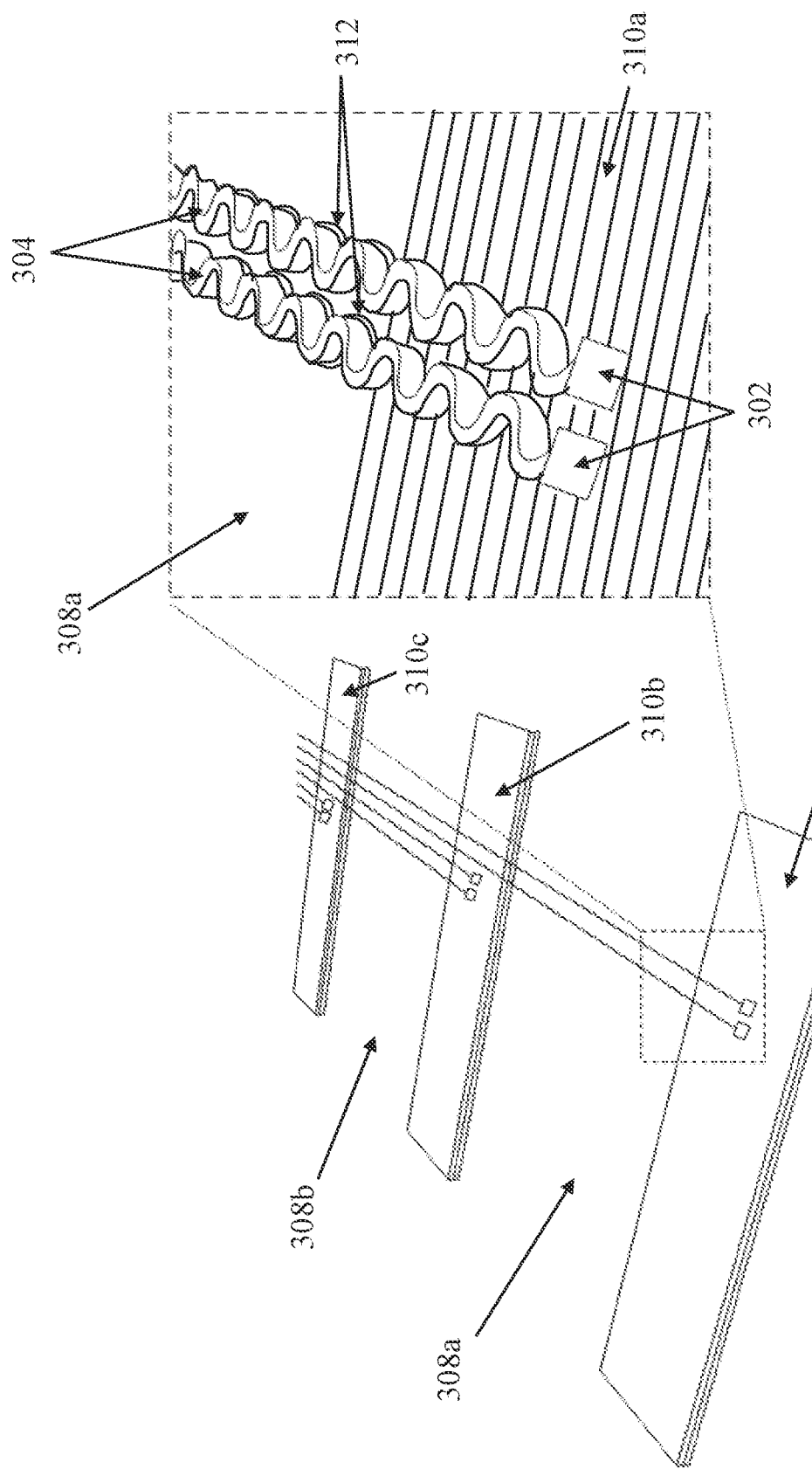

Referring now to FIG. 3B, the laser cutter 314 is moved according to the raster path illustrated by the dashed lines within region 308 while applying a laser beam to the top surface of the PCB 300. Applying the laser beam according to the raster path causes the insulation material of the insulation layer 306 to be removed within region 308. Referring to FIG. 3C, the insulation material (e.g., polymer) is now removed from regions 308a and 308b by further applying the laser beam, according to another raster path within region 308b, to the top surface of the PCB 300. The insulation layer 306 is maintained within regions 310a, 310b and 310c. The serpentine or flexuous shapes allow the electrically conductive structures 304 to stretch, especially within regions 308a and 308b where the insulation layer 306 is removed.

As illustrated in FIG. 3C, the circuit components 302 or sensors can be located within regions 310a, 310b and 310c of the PCB 300 where the insulation layer 306 is not removed. In other words, regions where the insulation material is removed, e.g., regions 308a and 308b, can be selected, determined or identified as regions that do not include any of the circuit components 302 (or sensors). The circuit components 302 or sensors are distributed among the plurality of regions 310a, 310b and 310c. The portions 312 of the insulation region 306 that are beneath the electrically conductive structures 304 are maintained within region 308a after applying the laser beam to the surface of the PCB within region 308a. The same applies to region 308b where the laser beam also applied. The portions 312 can be viewed, and referred to, as connectors 312 that are made from the insulation layer 306.

The flexible circuit 316, obtained after removing the insulation material at least within regions 308a and 308b, includes a plurality of portions or blocks 310a-310c of the insulation layer 306. The portions or blocks 310a-310c include circuit components 302. Each portion or block is connected to an adjacent portion or block via one or more connectors made from the insulation layer 306. For instance, portion or block 310a of the insulation layer 306 is connected to portion or block 310b of the insulation layer 306 via the connectors 312. The flexible circuit 316 includes electrically conductive structures 304 that are deposited on and defining a top surface of the connectors 312. The electrically conductive structures 304 extend between and across the plurality of blocks 310a-310c. The portions or blocks 310a-310c can include a plurality of insulation layers. For instance, the circuit components 302 and/or the electrically conductive structures 304 can be integrated between two or more insulation layers within portions or blocks 310a-310c. In such case, the connectors 112 are made of insulation layer(s) that is/are beneath the circuit components 302 and the electrically conductive structures 304. The circuit components 302 can include sensors, in which case the flexible circuit can be viewed as a flexible sensor array.

Figure 3D:
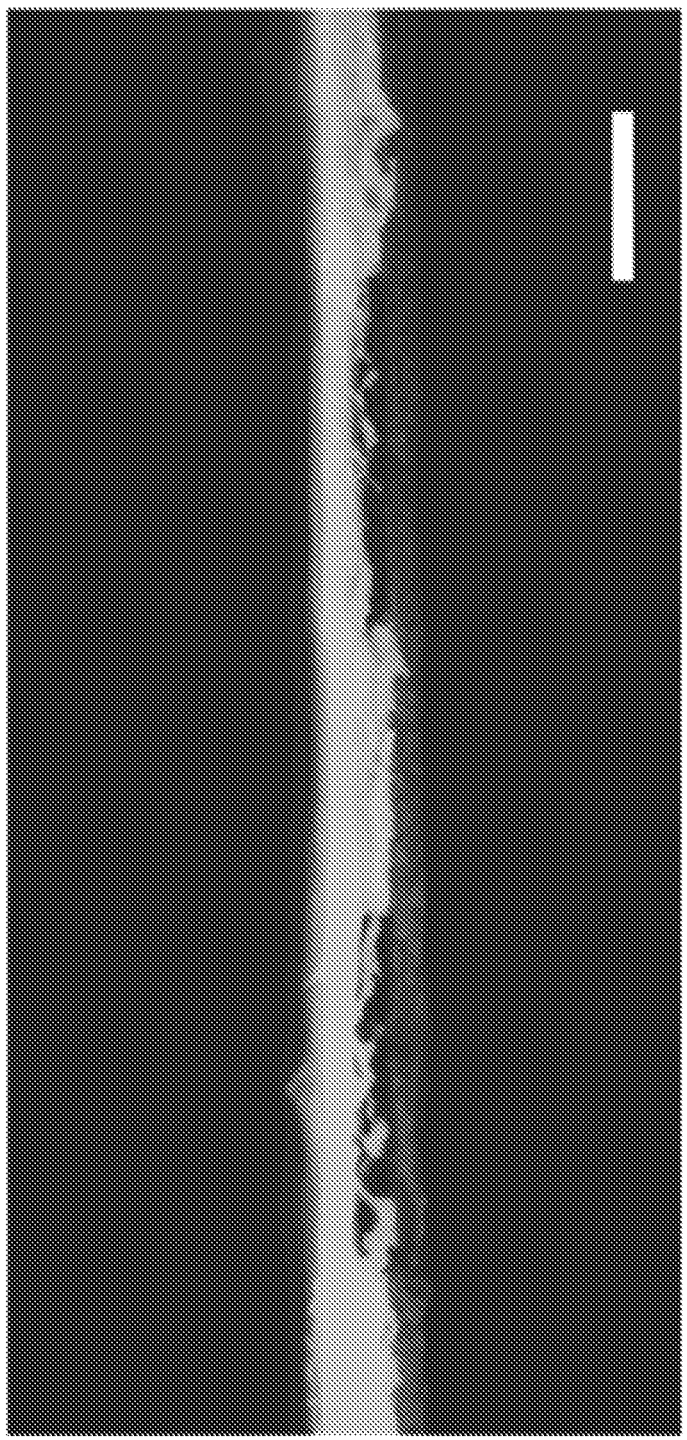
Figure 3E:
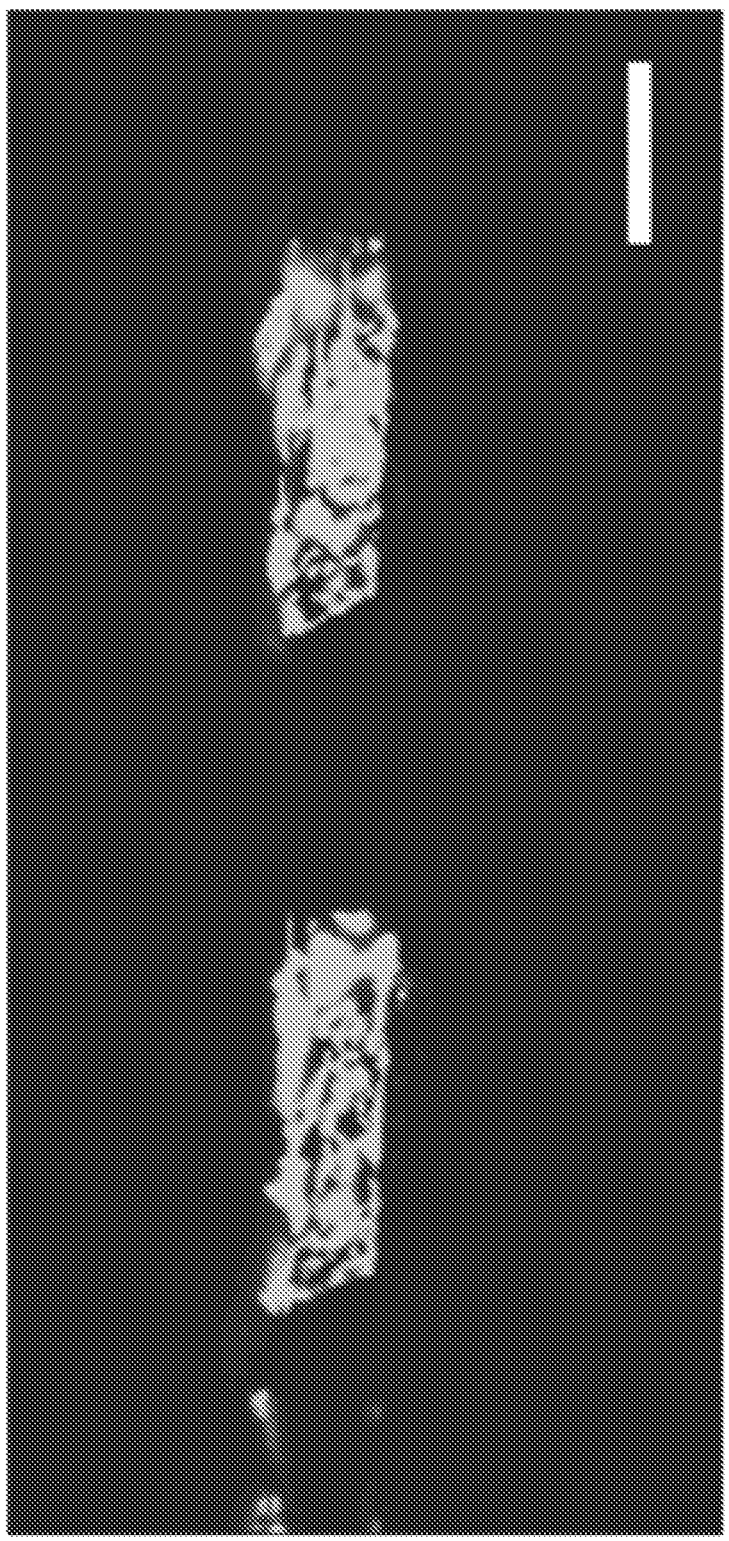
Figure 3F:
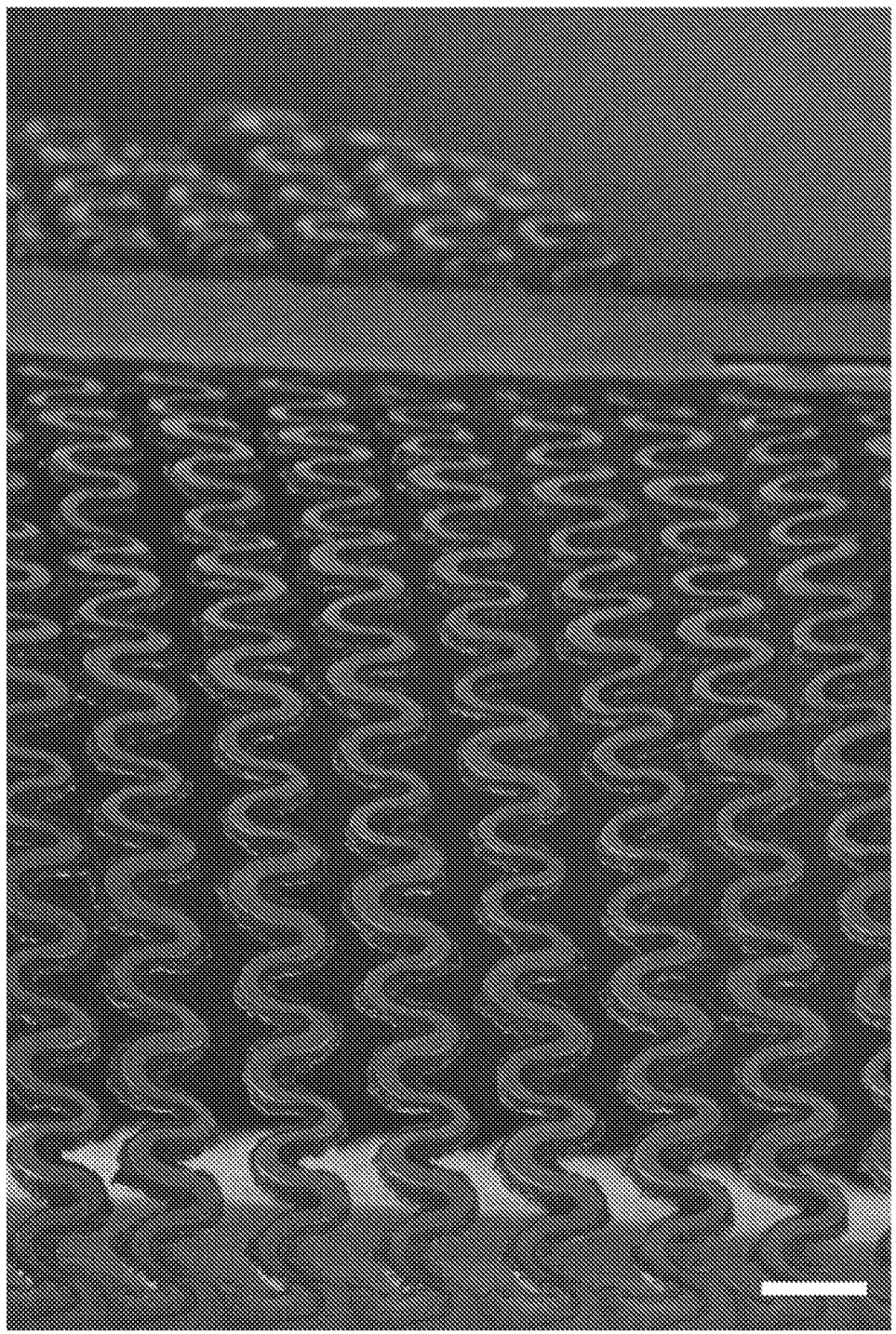
Figure 3G:
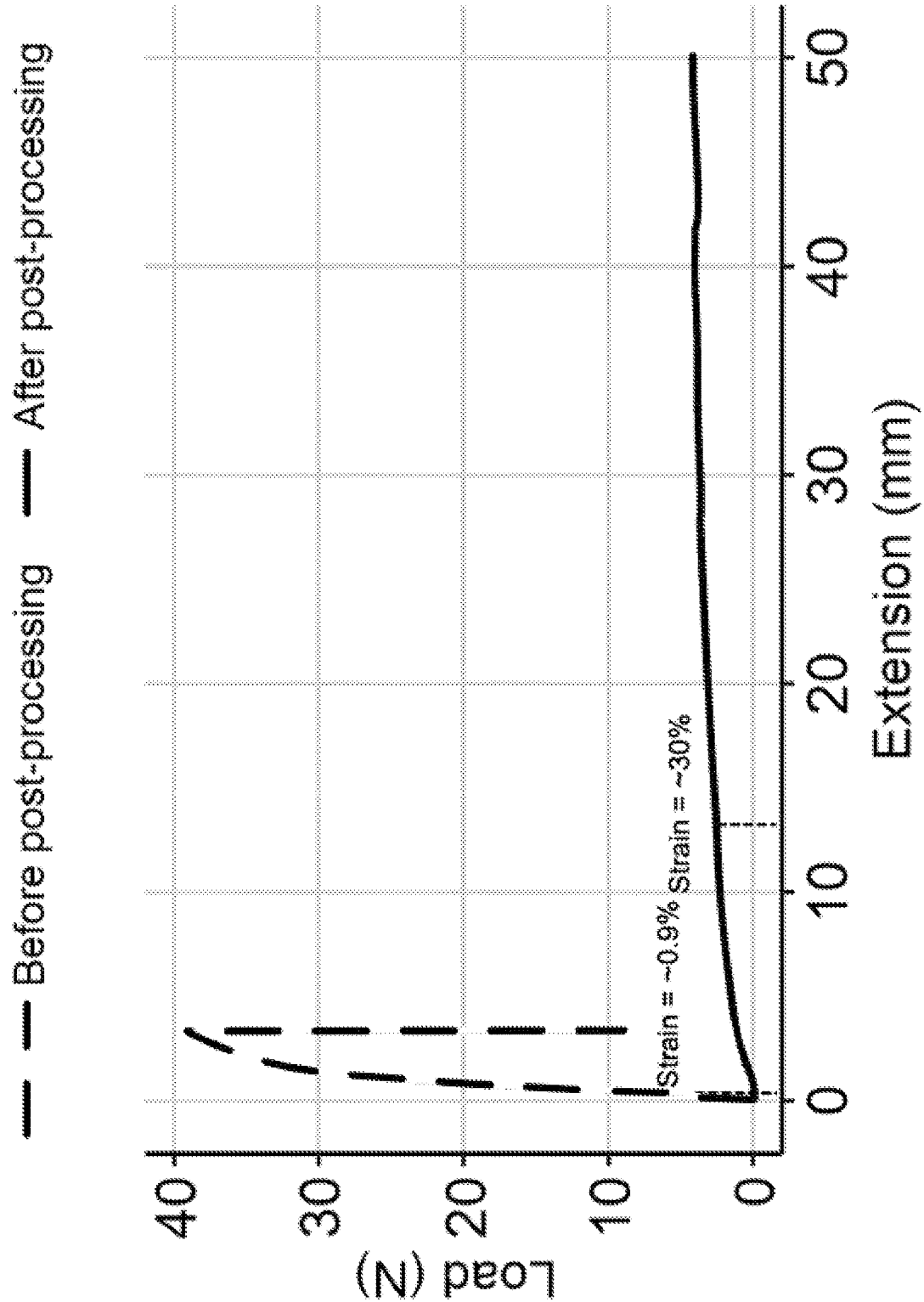

Experimental tests were performed on the flexible circuit 316 and the PCB 300 to assess the efficiency and reliability of the selective removal of the insulation layer(s) 306. The results are shown in FIGS. 3D-3G. FIG. 3D shows a cross sectional (end on) confocal image of the electronics, or PCB 300, before laser cutting. The scale bar, shown in white, in the confocal image of FIG. 3D is 0.1 mm long. FIG. 3E shows a cross sectional (end on) confocal image of the electronics, or PCB 300, after laser cutting. The scale bar, shown in white, in the confocal image of FIG. 3E is 0.1 mm long. FIG. 3F shows a scanning electron microscope (SEM) image of the final laser cut stretchable circuit. The central region of the SEM image depicts a region of the PCB where the insulation material was removed. The scale bar, shown as a white rectangle, in the SEM image is 0.3 mm long. FIG. 3G shows results for a tensile test before and after selective removal of the insulation layer(s) 306. The enhanced stretchability of the post-processed circuit (or sensor array) 316 can be clearly observed.

According to various embodiments, the flexible electronics (or flexible PCB) 300 may be manufactured initially in a flex house (PCB universe), for example, to ensure scalable production. The design may comprise two or more layers. These layers can include a layer of electrically conductive (or metallic) structures, e.g., copper or other metallic traces, that is deposited on an insulation layer (or polyimide (PI) layer) or may be sandwiched between two or more insulation layers (e.g., PI layers). In various embodiments, the electrically conductive structures may comprise serpentine traces connected to, for example, electrodes on each flexible circuit board. The selective removal of the insulation layer(s) provides windows, sections or regions where the electrically conductive structures are exposed for contact. In various embodiments, the thickness of the insulation layer (e.g., PI layer) may be, for example, between about 15 μm and about 75 μm. Also, the thickness of the electrically conductive structures (e.g., copper traces) may be, for example, between about 15 μm and about 75 μm. As such, the flexible PCB (or PCB) may initially have a uniform thickness of, for example, between about 30 and 150 μm. The stretchability of the flex PCB may be a direct function of its thickness.

A laser (e.g., CO2 laser (Universal Laser, power 23%, speed 50%)) may be used to selectively remove the insulation material (e.g., PI or polymer) from sections or regions (e.g., regions 308a and 308b) of the flex PCB as shown in FIGS. 3B and 3C. The laser, or heat source, may raster as indicated by dashed lines in FIG. 3B thereby removing the insulation material (e.g., PI or polymer) from the regions to which thermal energy or the laser beam was applied.

In various embodiments, working conditions (or settings) of the heat source or laser 314 may be optimized to preserve or maintain the insulation material (e.g., PI or polymer) underneath the electrically conductive structures 304 (e.g., metallic/copper traces). The selective removal process makes use (or takes advantage) of thermal masking, whereby the electrically conductive structures (e.g., metallic/copper traces) allow for heat applied to them to be rapidly spread, therefore reducing peak temperatures, and preventing the underlying insulation layer(s) (e.g., PI or polymer layers) from reaching temperatures sufficient for removal. Meanwhile, regions of insulation layers (e.g., PI or polymer), which are usually thermally insulating, that are directly exposed to the heat source and are not beneath (or in contact with) the thermally conductive metallic structures (e.g., copper traces) may reach higher peak temperatures and may be subsequently removed.

The selective removal process can be referred to as a self-aligned thermal energy based (or laser based) conversion approach. Simulations were made and various simulation parameters were look examined to explore the effect of thermal masking in the self-aligned thermal energy based (or laser based) conversion approach. A single pulse ablation model was applied, and the energy density and fluence distribution of a Gaussian laser beam were simulated on sections of the flex-PCB. The simulation results for studying the working conditions (or settings) of the heat source or laser, thickness of layers, and the resolution of this approach comprehensively using this model to elaborate on factors to be considered to employ this technique for large scale processing.

Figure 4A:
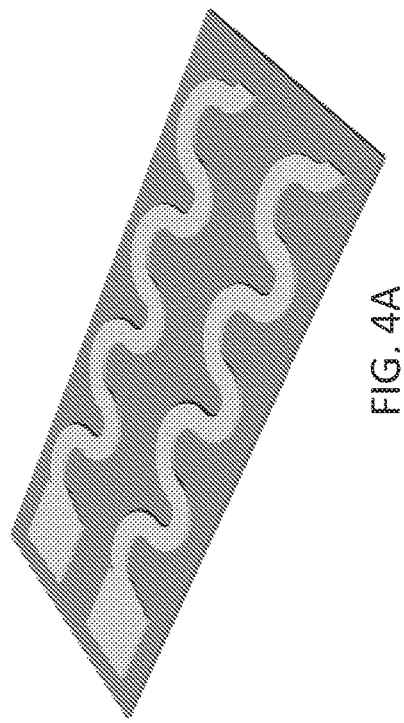
FIG. 4A-4B depict a sample flexible PCB and corresponding simulation and experimental results illustrating material removal temperatures for a single pulse of various powers, according to example embodiments of the current disclosure.

Referring to FIG. 4A, two representative, adjacent serpentine traces are modeled in the simulation which contain two electrodes at their ends (e.g., for connecting to circuit components such as sensors). Serpentine traces are chosen in the simulation since they offer maximum stretchability. A layer of polyimide is modeled in contact with copper traces. The thermal conductivity is defined based on a harmonic mean. All other material properties including specific heat and density are defined as well. Insulation on the bottom service of the flex-PCB was applied, and a convective boundary was also applied across all the faces of the model. Initially two regions of interest identified, and point Gaussian heat flux was applied in these regions to observe the temperature distribution. Note that a point Gaussian laser heat source is applied in this study in order to better calibrate the simulations with experiments and also reduce the inconsistencies associated with speed and pulse per inch (PPI) setting of the laser which are specific to the laser cutter used in our laboratory. The Gaussian beam profile of a laser beam can be defined as:

$$F(x, y, z) = F_o \cdot e^{-\left(\frac{x^2+y^2}{2\sigma^2} - \alpha \cdot z\right)}.$$

Where $F_o$ represents the peak fluence of the laser beam, $\alpha$ is the absorption coefficient and $\sigma$ is the width which comes from the following equation $$4\sigma = d_{min} = 2.44\frac{fM^2\lambda}{D}.$$

The parameter $d_{min}$ is the position, where the intensity drops to $1/e^2$ and f is the focal distance, D is the beam diameter, $M^2$ is the beam quality parameter, and $\lambda$ is the wavelength of the Gaussian beam. The relation between absorption coefficient and temperature is given as $$\alpha = 8.10^3 - 10(T - 300) \text{ in } \left(\frac{1}{m^3}\right).$$

Figure 4B:
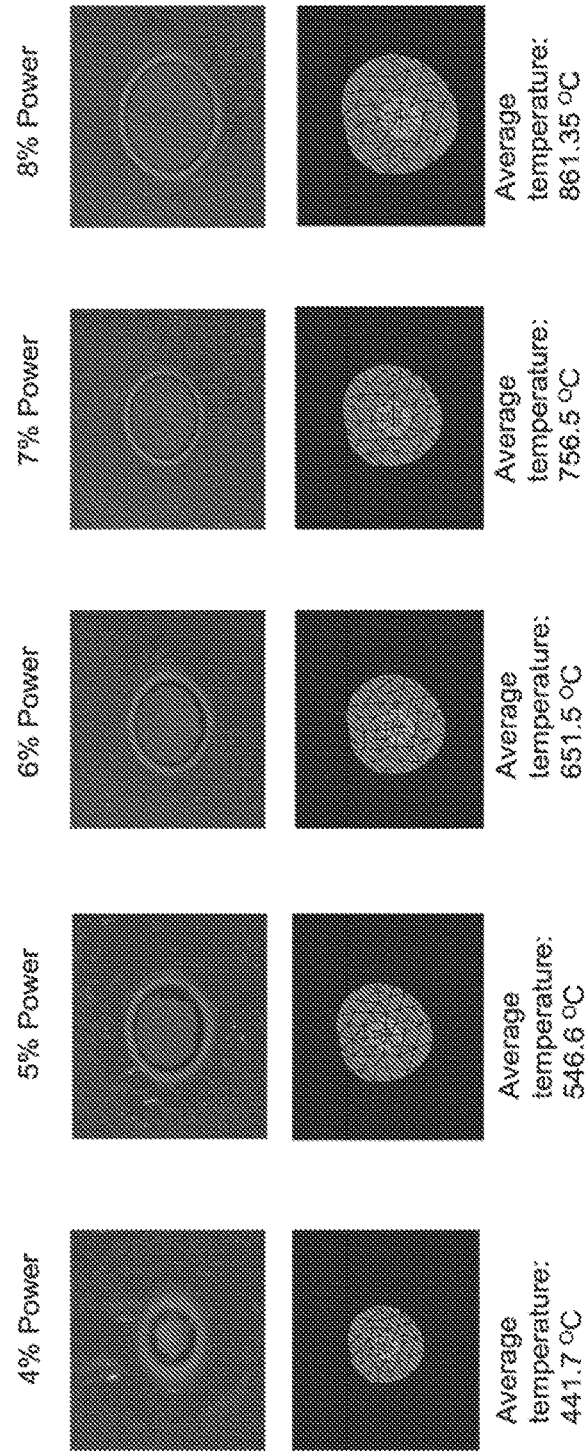

Using these parameters, a custom code was used to define a Gaussian beam pulse on a desired location on the model. A single pulse was chosen to order to minimize the inconsistencies associated with speed, and PPI parameters which are unique to a certain laser cutting system and the way certain systems are designed to maintain these parameters. In order to verify if these models are accurate, calibration experiments were conducted using the Universal laser. The laser beam used in these experiments have a maximum power 30 W and all the power values mentioned in this study are a percentage of this total power. Referring to FIG. 4B, simulation and experimental results illustrating material removal temperatures for a single pulse of various powers, are shown. The experimental material removal temperatures correspond to material removal temperatures observed the simulations, which validates the simulation model.

In the calibration experiments, a standard CO2 laser (universal laser) is used, and single pulses were applied on regions of the flexible PCB consisting of only Kapton and Kapton & copper. Similar single pulses were simulated using the model described earlier. Knowing the decomposition temperature of Kapton to be 520 OC, the average temperature from the simulation heat map can be compared with Kapton removal from the experiment to calibrate the simulations.

Figures 5A, 5B:
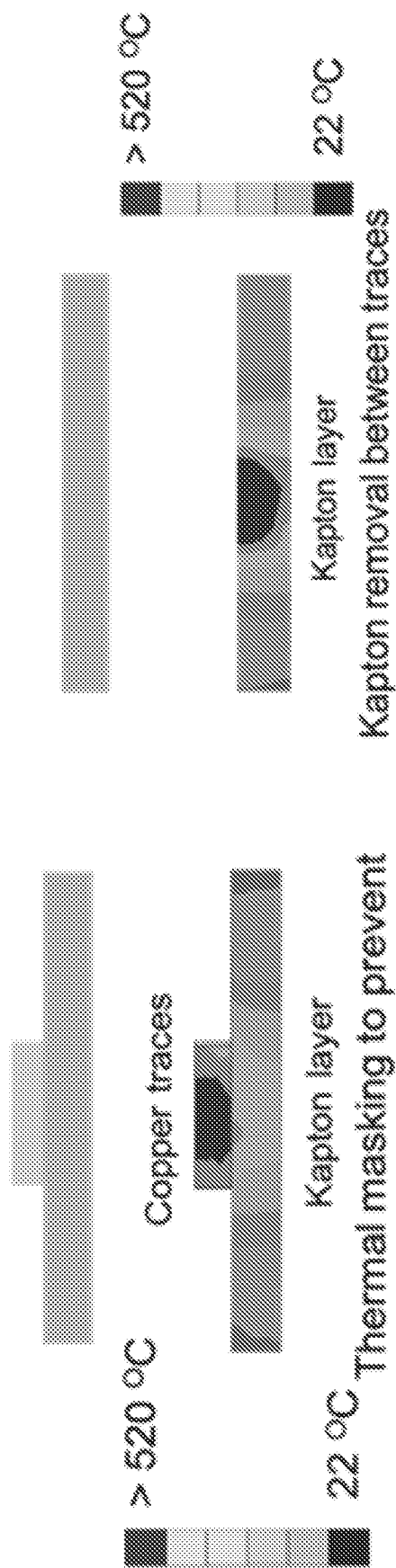

Upon validating the model, simulations were run for varying thicknesses of copper and Kapton exposed to various laser pulse powers in order to elucidate under what conditions self-aligned removal can be achieved and when it does not. FIGS. 5A and 5B show the heat maps for a region where thermal masking phenomenon occurs, and a region where only bare Kapton exists.

It should be appreciated that the output and application of the thermal energy source can be calibrated, fine-tuned or configured based on various factors. In particular, a distance between the thermal energy source from which the thermal energy is emitted and the PCB surface to which the thermal energy is applied can be selected to successfully remove the insulation material. In addition, the amount of thermal energy emitted from the heat source can also be selected. The distance and the amount of thermal energy to select can be based on the thickness of the electrically conductive structures and the thickness of the insulation material to be removed as well as the decomposition, melting and/or state change temperatures of the insulation material and the electrically conductive structures. The goal of the selection or determination of the conditions or parameters for applying the thermal is to achieve the desired selective removal of the insulation material, such that the insulation material is removed within given regions of the PCB except beneath the electrically conductive structures 304.

Figure 5C:
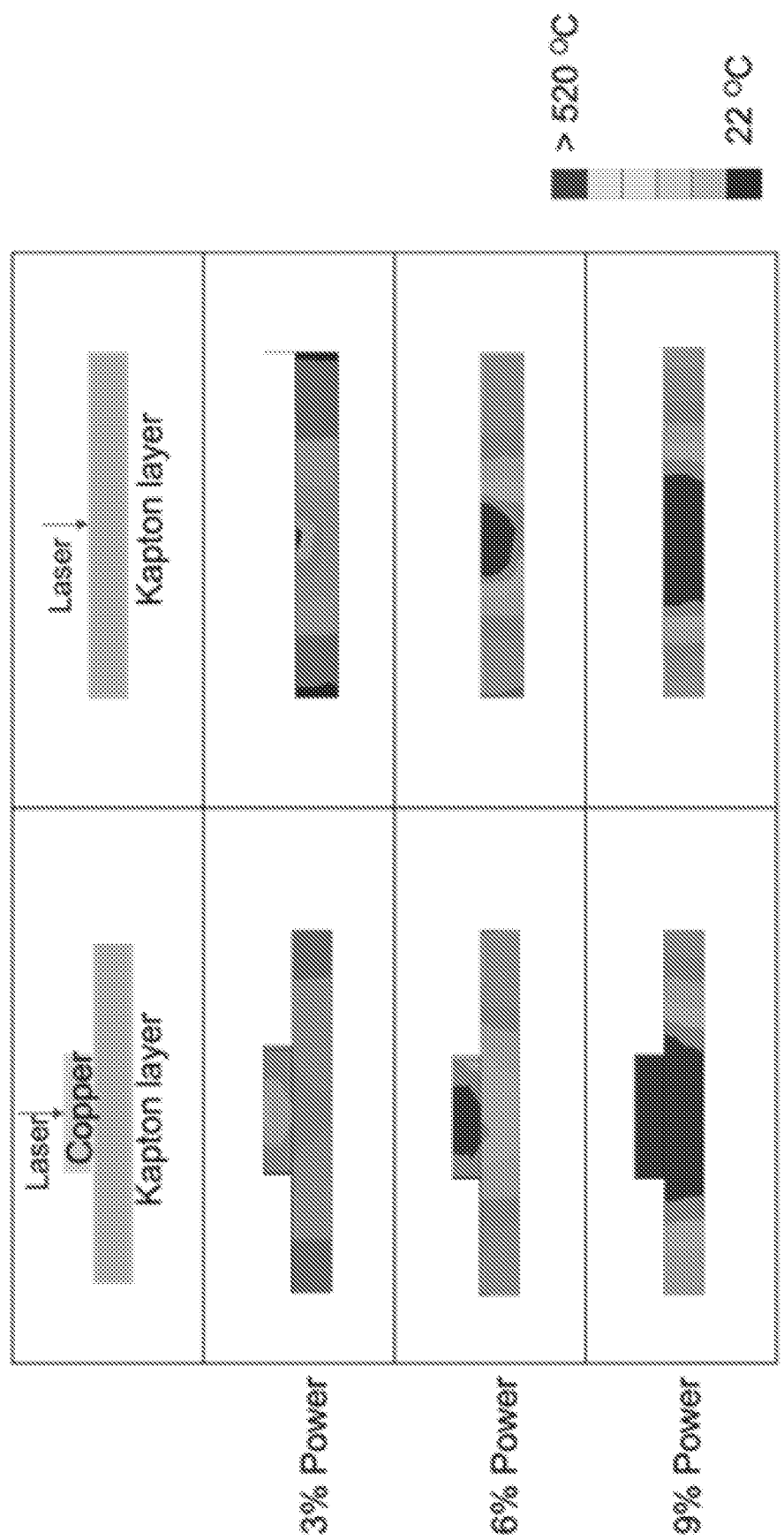

Referring to FIG. 5C, heat maps for under-heating, optimal and overheating conditions for the self-aligned material removal process are shown. During the under-heating condition, the temperature of bare Kapton remains below Kapton decomposition temperature. In the optimal condition, the temperature of bare Kapton is above the decomposition temperature. However, the temperature of Kapton below the copper is under the decomposition temperature. The overheating condition can be subdivided into two regimes. When the temperature of Kapton underneath copper is above the decomposition temperature but the temperature of copper is below its melting point, and when the temperatures of both Kapton and copper are above their respective decomposition and melting points.

A processing window is defined as the set of conditions (sample geometry, laser power, etc.) where self-aligned removal is achieved successfully. This can be evaluated by conducting thermal simulations for a wide variety of conditions. FIG. 5D shows the processing window for varying copper thicknesses. The boundaries of this plot are determined by obtaining conditions where the process fails in one of three conditions, which are (i) when the temperature is lower than decomposition temperature for Kapton in bare Kapton region, (ii) when the temperature of Kapton below the copper traces is above the decomposition temperature, and (iii) when the temperature of copper is above its melting point. While describing the processing window for a specific thickness of copper and Kapton, these conditions determine the limits up to which this process can be employed.

Figure 6A:
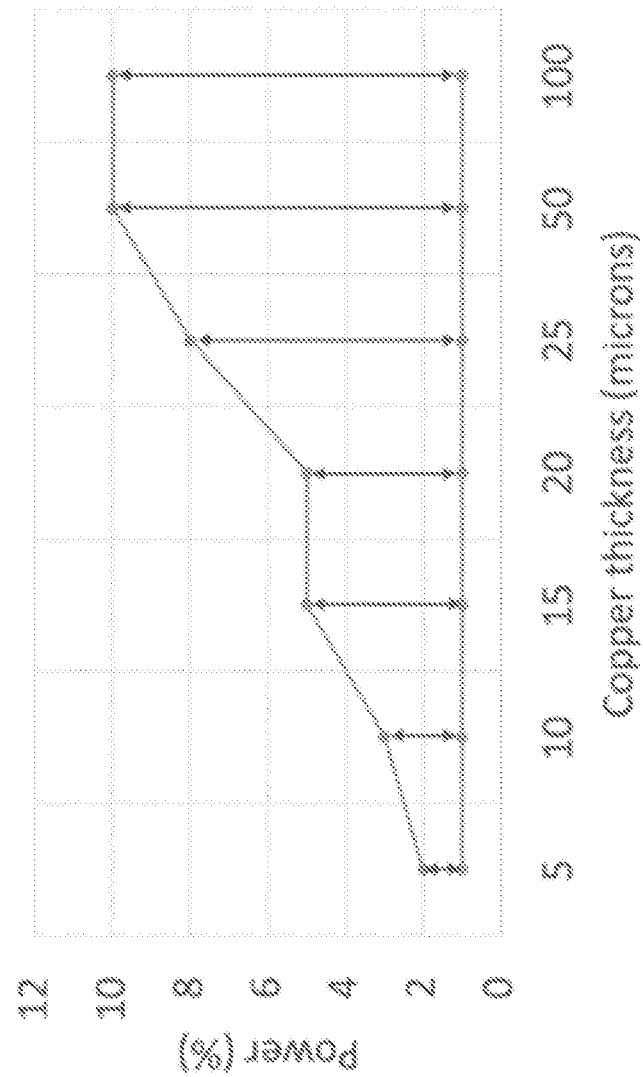
FIGS. 6A-6E depict experimental and simulation results illustrating processing windows, with respect to thickness and resolution of metallic structures to achieve successful self-aligned removal, according to example embodiments of the current disclosure.
Figure 6B:
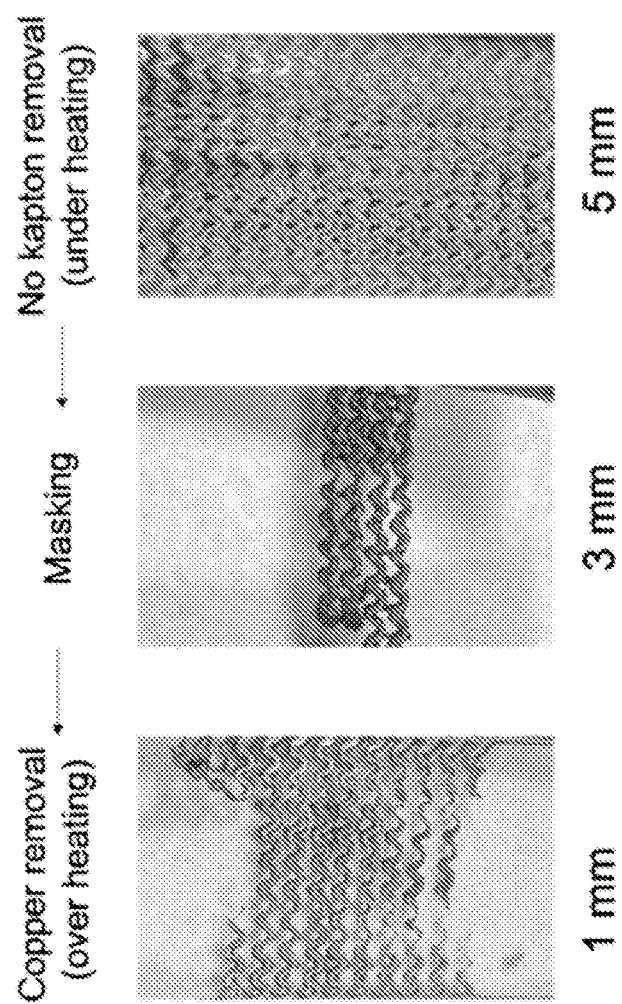

FIG. 6A shows the processing power window as a function of copper thickness, which is an indication of how sensitive the success of the process is to input power provided by the laser. As illustrated by the plot in FIG. 6A, it is easier to achieve self-aligned laser based conversion successfully for samples with thicker copper (or electrically conductive) traces. This is mainly because with increasing copper thickness, the critical power required for overheating increases, thereby giving a larger processing power window. The processing power window is also critical because a variety of factors influence the power that is actually delivered to the sample, such as the z-axis alignment between the laser and the sample. The larger the power processing window, the easier it is to achieve uniform self-aligned selective laser removal, over the entire sample without the need for high precision tools. To illustrate this effect, the same laser cutter used in the calibration experiments (Universal laser) was used to make multiple cuts by varying the z-values as shown in FIG. 6B. The z-values represent the distance between the laser cutter and the surface of the PCB to which the laser beam is to be applied. This demonstrates the process moving from under-heating to optimal to overheating with varying z values. Therefore, there exist optimal z values where the process is most effective. This highlights the need for larger processing windows so as to accommodate for z axis variations that might present during the process.

In the z-axis experiments, an inclined ramp with height varying between 1 mm and 5 mm was 3D printed in the lab and the flexibled PCB was mounted on the ramp. Based on the desired height, a series of linear cuts were programmed on the laser cutter at the specified location along the ramp.

Figure 6C:
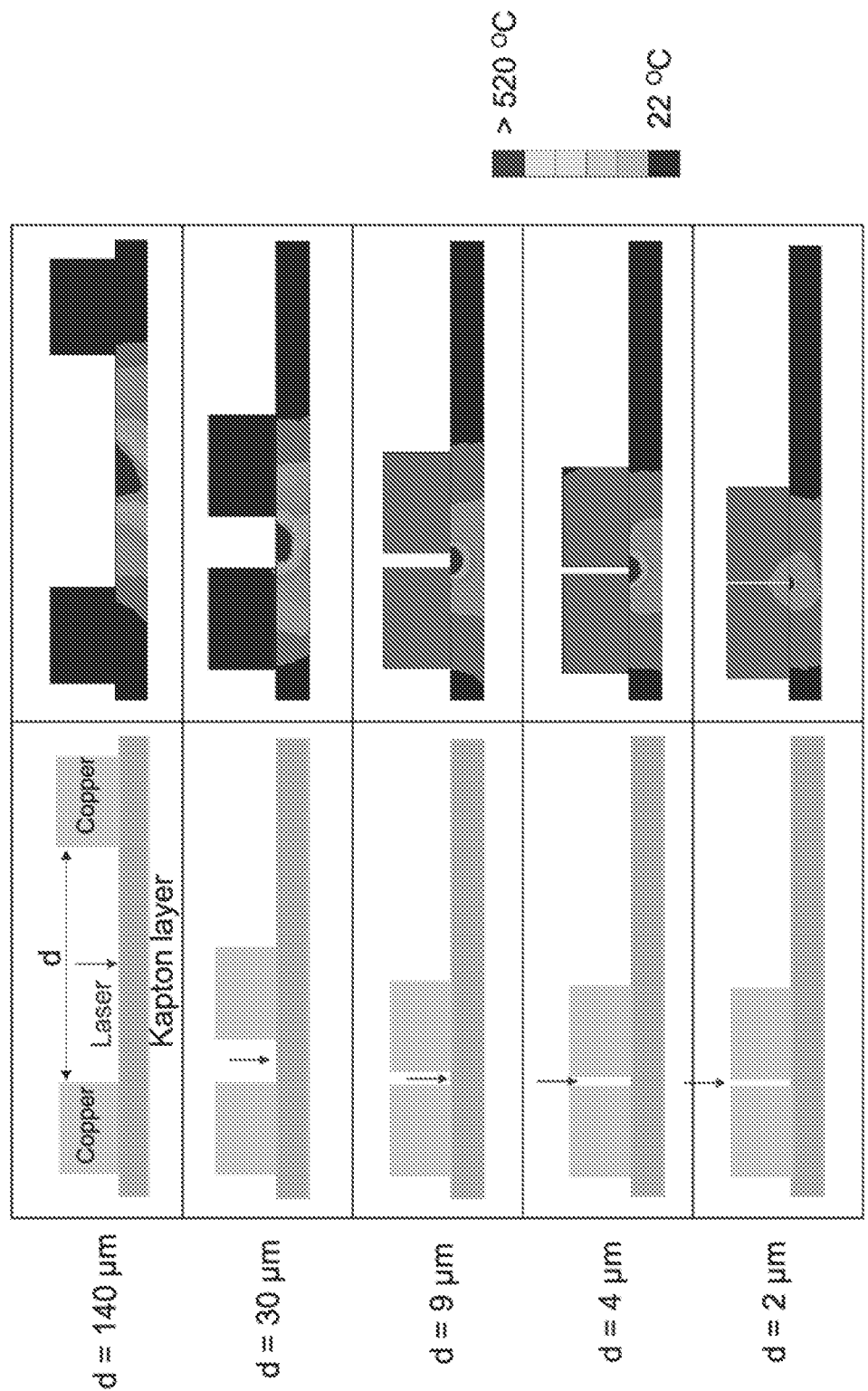

Another key parameter that is worth highlighting while designing the flex-PCBs and employing this process is the resolution or distance between the traces. This is important because it determines the sample geometries for which this process can be reliably applied. An analysis was performed with linear trace geometries. Referring to FIG. 6C, the samples in column 1 illustrate the effect of trace spacing schematically. In order to demonstrate the effect of resolution on process parameters, a point is chosen on FIG. 4A (20 μm thickness of Kapton and 40 μm thickness of copper). Column 2 in FIG. 6C shows the heat maps when the laser beam (6% power) is irradiated at a central point between the two traces (d/2).

Here, when trace spacing is large, the heating in the region between traces is not impacted by the electrodes, and the behavior observed is similar to the examples discussed above. As the traces move closer together they begin to partially mask the laser spot, reducing the energy delivered to the Kapton between the traces for removal. The resulting effect is to increase the power required to achieve complete removal, thus narrowing the power processing window.

Figures 6D, 6E:
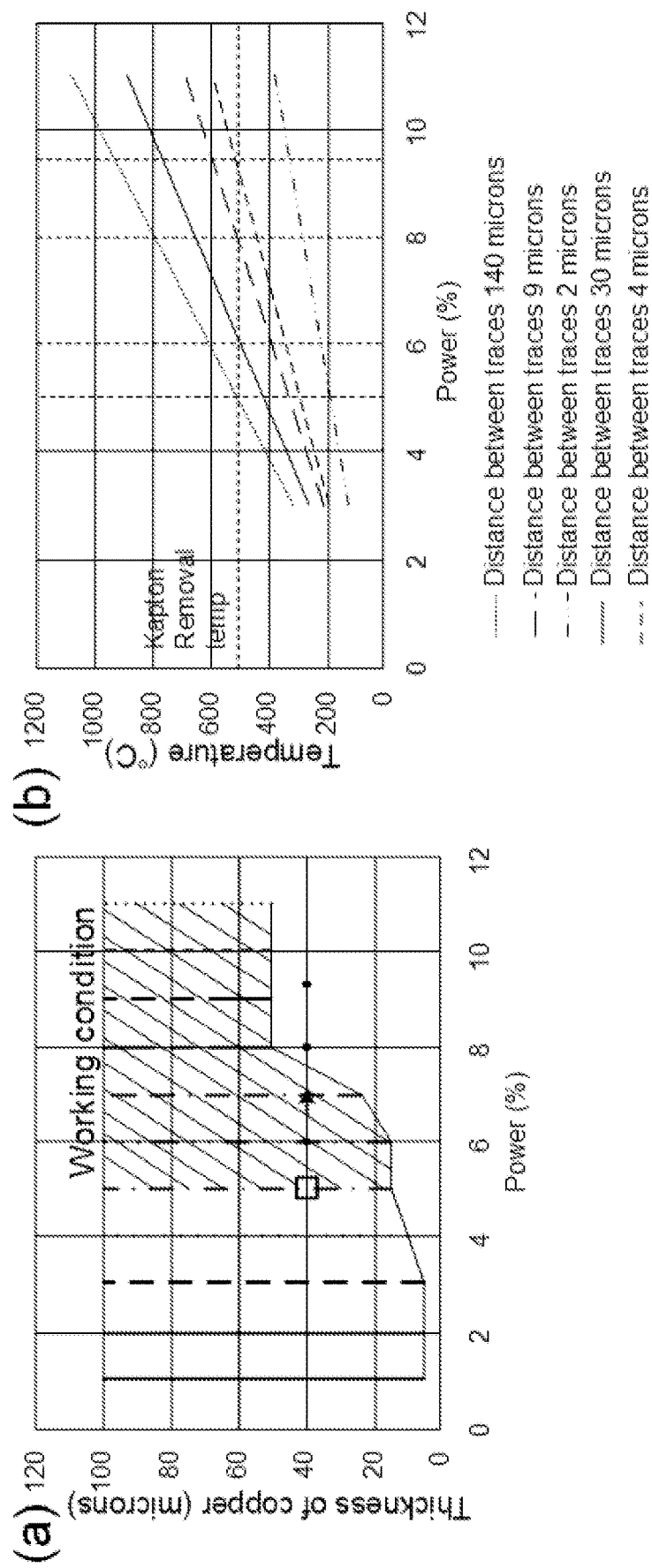

The effect of resolution on working conditions is shown in FIGS. 6D and 6E. FIG. 6D is an adaptation of FIG. 5D (processing window) to indicate the effect of trace spacing. For very large trace spacing, the left sided boundary of the processing window is the same as observed in FIG. 5D and is defined by the Kapton thickness. The small box or square shows the data point that corresponds to a large spacing, e.g., 140 μm. As the spacing is reduced, masking from the electrodes reduced the laser energy that reaches the substrate, requiring higher power and moving the left sided boundary of the processing window to higher power. For spacing between 30 and 9 μm, the left boundary moves past the right hand boundary, indicating that for this Kapton and Cu thickness, self-aligned removal cannot be achieved. The decomposition temperature of Kapton is also indicated in the plots of FIG. 6E. At powers above the intersection points between the Kapton decomposition and the temperature curves, the Kapton underneath is removed. Therefore, this region is not in the workable range for this process. This phenomenon is also highlighted in FIG. 6E where, according to these intersection points, the original point for 20 μm thickness of Kapton and 40 μm thickness of copper moves to the right until it moves out of the processing window. Therefore, this is defined as the limiting factor for resolution of traces that can be used for this laser post-processing technique.

Referring back FIG. 2, the method 200 can include determining an output thermal energy range of the heat source to cause the insulation material of the insulation layer to be removed from the region while maintaining the portion of the insulation layer beneath the one or more electrically conductive structures, and setting the heat source to generate the thermal energy according to the output thermal energy range prior to applying the thermal energy to the surface of the PCB. While the simulation and experimental results in FIGS. 5A-5B and 6A-6E relate to the use of a laser cutter and applying a laser beam, the same concept of thermal masking also applies for other types of heat sources. The output thermal energy range can be determined based on simulation results and/or experimental results.

The output thermal energy range can be determined based on a first temperature specific to the insulation layer and a second temperature specific to the one or more electrically conductive structures. The first temperature specific to the insulation layer can represent a removal temperature of the insulation layer when the thermal energy is directly applied to the insulation layer. Such temperature can include, for example, a decomposition temperature, a sublimation temperature, an ablation temperature, a spallation temperature or a melting temperature of the insulation layer. The output thermal energy range can be determined based a third temperature that represents a removal temperature of the insulation material beneath the electrically conductive structures. The second temperature specific to the one or more electrically conductive structures can represent a melting temperature, an oxidation temperature or a phase change temperature of the electrically conductive structures. As discussed above with regard to FIGS. 6A-6E, the output thermal energy range can be based on a thickness of the insulation layer and/or a thickness of the one or more electrically conductive structures.

In the case where the heat source is a laser cutter, the method 200 can include determining an output power range of the laser cutter to cause the insulation material of the insulation layer to be removed while maintaining the portion of the insulation layer beneath the one or more electrically conductive structures, and setting the laser cutter according to the output power range prior to applying the laser beam to the surface of the PCB, as discussed above with regard to FIGS. 6A-6E.

The selective removal process can be viewed as a self-aligned removal process because it allow for accurate alignment between the electrically conductive structures and the insulation material maintained beneath the electrically conductive structures within the regions where thermal energy was applied. The boundaries of the electrically conductive structures and those of the insulation material maintained beneath the electrically conductive structures can be aligned along a depth direction of the original insulation layer (before material removal). The self-aligned removal process allows provides accurate alignment even with a relatively low cost laser or heat source.

The material removal process allows for exposing the one or more electrically conductive structures within the one or more regions where thermal energy is applied, to sense electrical voltage of a surrounding environment. The maintained portions of the insulation layer beneath the one or more electrically conductive structures allows the one or more electrically conductive structures, and the flexible circuit 316 as a whole, to maintain mechanical integrity within the region.

The initial PCB can include a plurality of insulation layers. In such a case, the thermal energy can be applied, within each region of the one or more regions, to the surface of the PCB, such that insulation material of the plurality of insulation layers is removed from the region while a portion of one or more insulation layers beneath the one or more electrically conductive structures is maintained.

Figure 7:
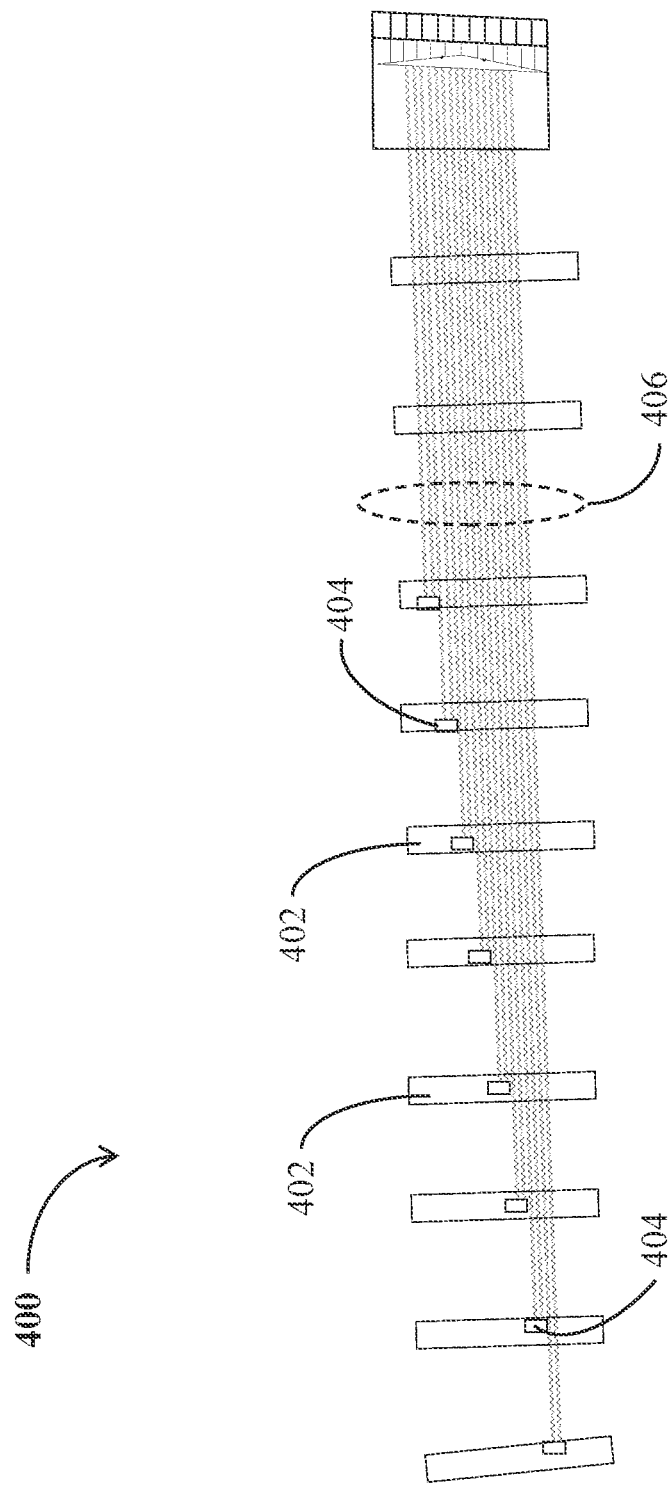
FIG. 7 depicts an example flexible/stretchable circuit, according to example embodiments of the current disclosure.

Referring to FIG. 7, an example flexible/stretchable circuit 400 is shown, according to example embodiments of the current disclosure. The flexible circuit 400 can include a plurality of portions or blocks of an insulation layer 402. The blocks or portions 402 can include a one or more circuit components 404. Each block can be connected to an adjacent block via one or more connectors (not shown in FIG. 7) made from the insulation layer. The flexible/stretchable circuit 400 can include one or more electrically conductive structures 406 deposited on and defining a first surface of the one or more connectors. The one or more electrically conductive structures 406 can extend between and across the plurality of blocks 402. A connectors can be arranged beneath each electrically conductive structure 406.

The one or more circuit components 404 can include one or more sensors. For instance, the flexible/stretchable circuit 400 can be a flexible/stretchable sensor array. The sensors can be distributed among the plurality of blocks 402 of the insulation layer. The one or more electrically conductive structures 406 can include copper (or other metallic) traces. The insulation layer can includes a polymer or PI layer. The one or more electrically conductive structures 406 (or a portion thereof) extending between the plurality of blocks 402 can be exposed to sense electrical voltage of a surrounding environment. For instance, when such portions are in contact with, or in proximity to, to an organ tissue, the electrically conductive structures 406 can sense the electric voltage of the tissue.

In some implementations, a thickness of the insulation layer can between about 15 μm and about 75 μm, such as about 15 μm, about 20 μm, about 25 μm, about 30 μm, about 35 μm, about 40 μm, about 45 μm, about 50 μm, about 55 μm, about 60 μm, about 65 μm, about 70 μm or about 75 μm. In some implementations, a thickness of the one or more connectors can be between about 15 μm and about 75 μm, such as about 15 μm, about 20 μm, about 25 μm, about 30 μm, about 35 μm, about 40 μm, about 45 μm, about 50 μm, about 55 μm, about 60 μm, about 65 μm, about 70 μm or about 75 μm. In some implementations, a thickness of the blocks 402 can be between about 30 μm and about 140 μm, such as about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm or about 140 μm.

It is to be noted that properties of the flexible/stretchable circuit 316 discussed above with regard to FIGS. 3A-3G can also apply to the flexible/stretchable circuit 402. Also, the polymer layer or polymer substrate can include at least one of a urethane polymer, a polyurethane polymer, a copolymer, a silicone polymer, or an elastomer. Each exposed portion of the electrically conductive structure can detect a signal from one or more surfaces of a tissue structure (or other structure in proximity). Transmission lines can transmit the signals detected from each of the plurality of electrically conductive structures to an external measurement device through wired or wireless means. The flexible/stretchable circuit 400 may be manufactured or fabricated as discussed above with regard to method 200.

B. Soft Robotic Devices and Respective Manufacturing Processes

The flexible/stretchable circuits 316 and 402 discussed above in section A can be used to manufacture soft robotic devices, such as soft robotic sensor arrays (SRSAs) or other medical devices. The soft robotic devices described herein may have other applications other than medical applications.

Figure 8:
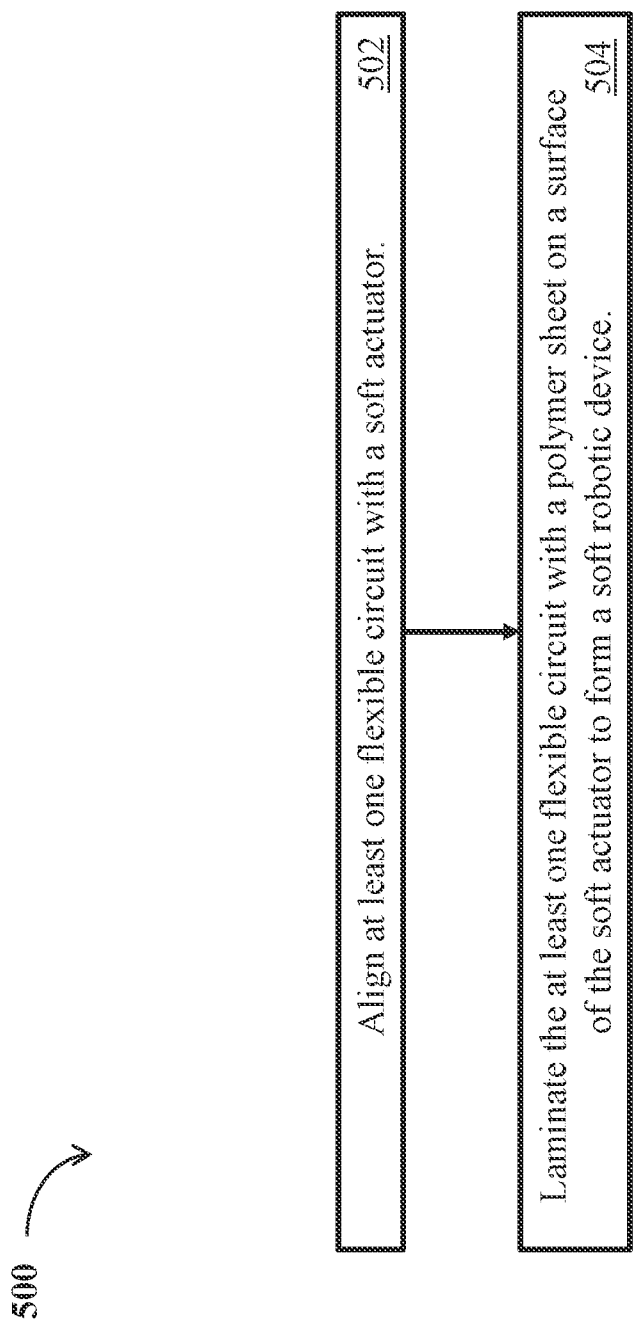
FIG. 8 shows a flowchart illustrating a method 500 of fabricating/manufacturing soft robotic devices, according to example embodiments of the current disclosure.

Referring to FIG. 8, a method 500 of fabricating/manufacturing soft robotic devices can include aligning at least one flexible circuit with a soft actuator (STEP 502). The method 500 can include laminating the at least one flexible circuit with a polymer sheet on a surface of the soft actuator to form a soft robotic device (STEP 504). The polymer sheet can be configured to provide, for the at least one flexible circuit, insulation and mechanical fixation to the soft actuator. As used herein, a soft actuator can be viewed, or can be referred to, as an inflatable actuator that is made of a deformable material.

Figure 9D:
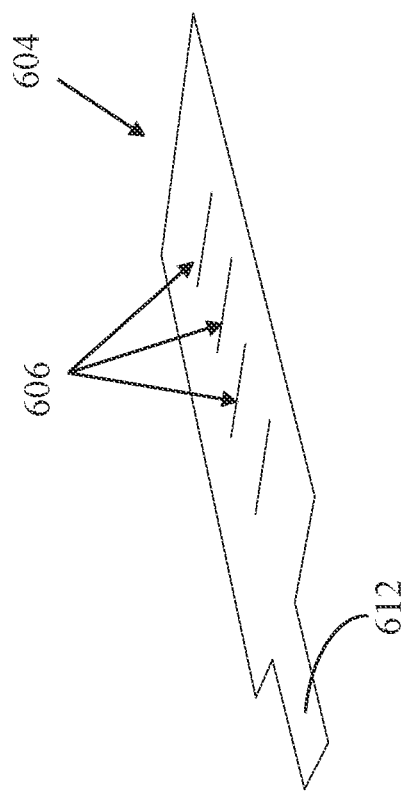

Referring now to FIG. 8 and FIGS. 9A-9H, the method 500 can include aligning the at least one flexible circuit with a soft actuator (STEP 502). FIGS. 9A and 9B show photographs of a manufactured flexible/stretchable circuit 602 and a manufactured linear bending soft actuator 604. The flexible/stretchable circuit 602 can be manufactured or fabricated as discussed above with regard to method 200. Each flexible circuit 602 of the at least one flexible circuits can include a plurality of blocks of an insulation layer including a one or more circuit components, and one or more electrically conductive structures deposited on and defining a first surface of the one or more connectors. Each block can be connected to an adjacent block via one or more connectors made from the insulation layer. The one or more electrically conductive structures can extend between and across the plurality of blocks. Aligning the at least one flexible circuit 602 with the soft actuator 604 can include arranging the at least one flexible circuit 602 on the soft actuator 604. The soft actuator can include, or can be made of nitinol or polymer such as polyurethane polymer or any other suitable material. The soft actuator 604 can include one or more indentations 606 to facilitate bending of the soft actuator 604, when the actuator is inflated. The indentations 606 can represent bending regions of the soft actuator 604. The flexible circuit(s) 602 can be similar to the flexible circuit 316 or 402 discussed in section A. The flexible circuit(s) 602 can be manufactured according to method 200.

Figure 9E:
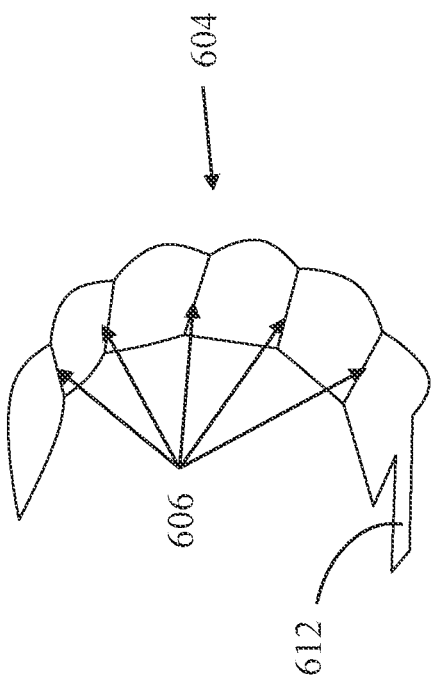
Figure 9C:
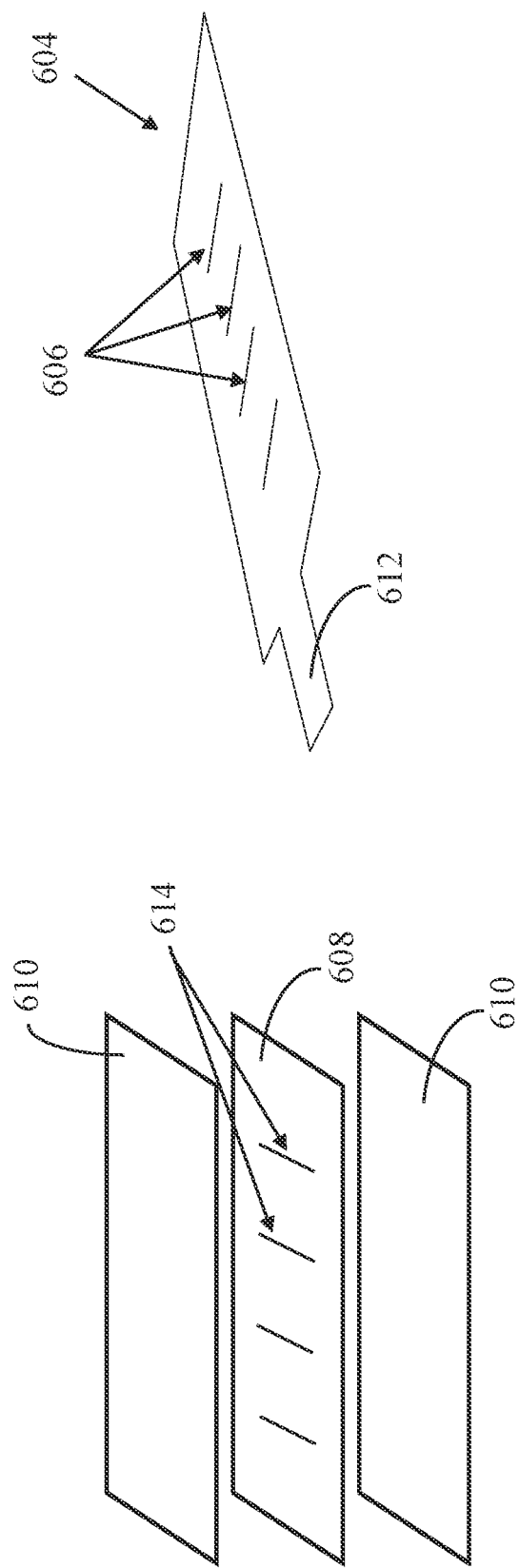

Referring now to FIGS. 9C-9E, diagrams illustrating an example process of manufacturing the soft actuator 604 using polymers are shown, according to example embodiments of the current disclosure. Manufacturing the soft actuator 604 can include laser cutting layers of polymer 610 and a sheet of water soluble polymer 608 according to desired shapes, arranging the sheet of water soluble polymer 608 between two or more layers of polymer 610, and thermally bonding (e.g., via heat press) the two layers of polymer 610 around respective borders. The sheet of water soluble polymer 608 can act as a sacrificial layer to form an inflatable closed channel between the two bonded layers of polymer. The inflatable closed channel can be inflated via the inlet or pressure line 612. FIG. 9D shows the soft actuator 602 in non-inflated state. FIG. 9E shows the soft actuator 602 when inflated, and illustrates how the indentations 606 facilitate bending of the soft actuator when inflated. The indentations 606 form bending regions along which the soft actuator 602 can bend easier than other regions. The indentations 606 can be distributed along a length of the soft actuator 604. The indentations 606 can be arranged transverse to a longitudinal axis or dimension of the soft actuator 604.

To achieve the indentations 602, the method 500 can further include making a plurality of cutouts 614 in the sheet of water soluble polymer 608, and thermally bonding the two layers of polymer 610 at the plurality of cutouts 614. The plurality of cutouts 614 can be distributed along a length (or a longitudinal dimension) of the sheet of water soluble polymer 608. The cutouts 614 can be arranged transverse to a longitudinal axis or longitudinal dimension of the water soluble polymer 608. In some implementations, the water soluble polymer can include polyvinyl alcohol.

Figure 9F:
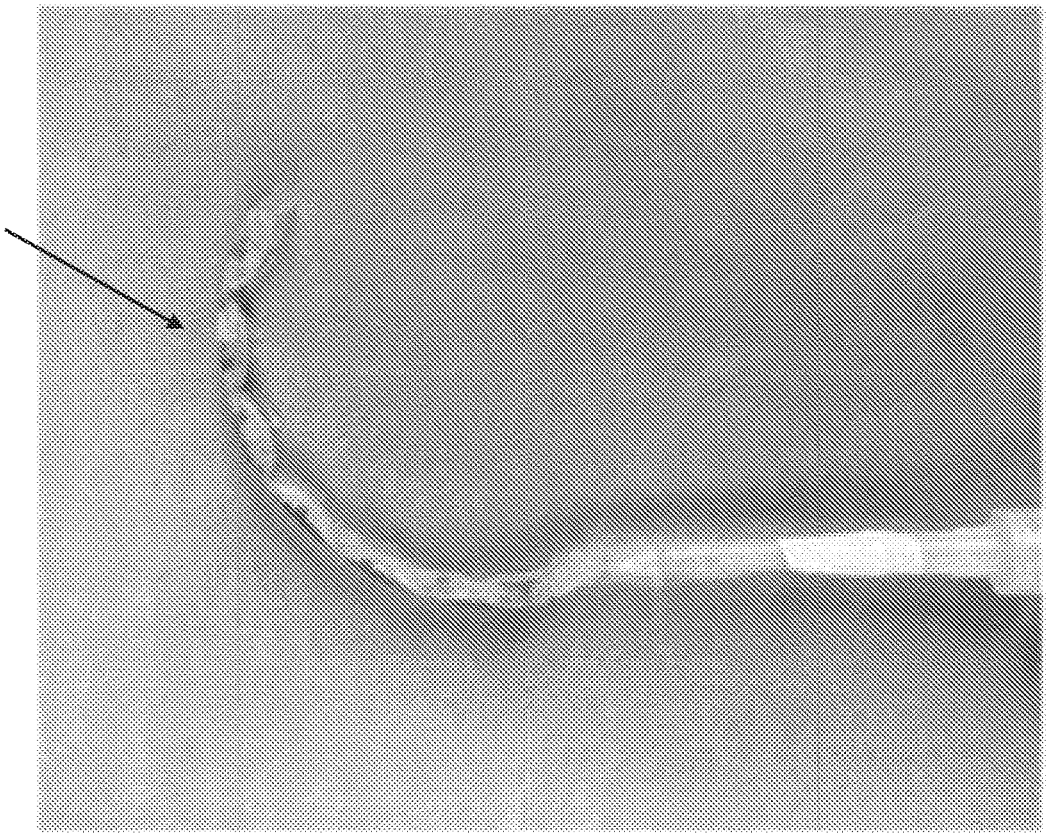
Figure 9F:
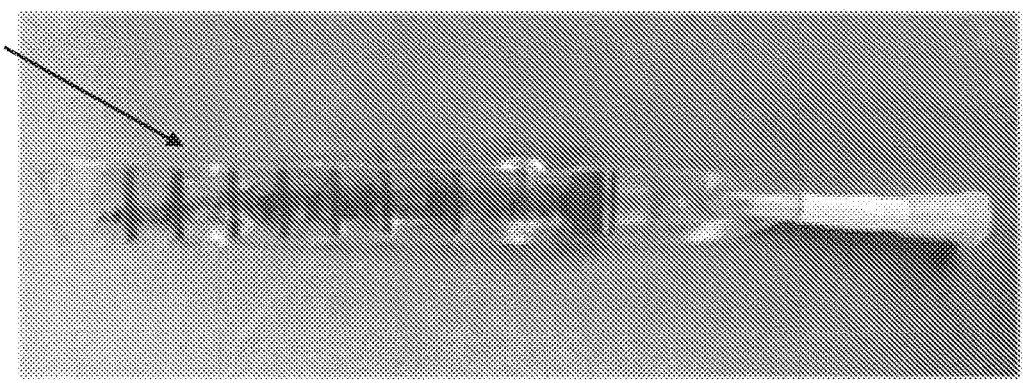

The method 500 can include laminating the at least one flexible circuit 602 with a polymer sheet on a surface of the soft actuator 604 to form a soft robotic device (STEP 504). The polymer sheet can be wrapped around one side (an outer side or surface) of the at least one flexible circuit 602 to attach, seal mechanical fixate the at least one flexible circuit 602 to the soft actuator 604. The polymer sheet can also provide an insulation to the soft actuator. FIG. 9F shows photographs of two sides of manufactured soft robotic device (or SRSA) 616. In some implementations, the polymer sheet can be, or include, a polyurethane sheet.

The method 500 can further include making one or more cutouts in the polymer sheet. The one or more cutouts can partially expose portions of the electrically conductive structures extending between the plurality of insulation layer blocks of the flexible circuit 602. Since the polymer sheet acts as an insulation, the cutouts allow for exposure of the electrically conductive structures to nearby environment, such as organ tissue. The one or more electrically conductive structures and the one or more connectors can have serpentine shapes. The one or more electrically conductive structures can include copper traces. Each connector of the one or more connectors can be substantially aligned with the conductive structure deposited on the connector as discussed above in section A.

Figure 9G:
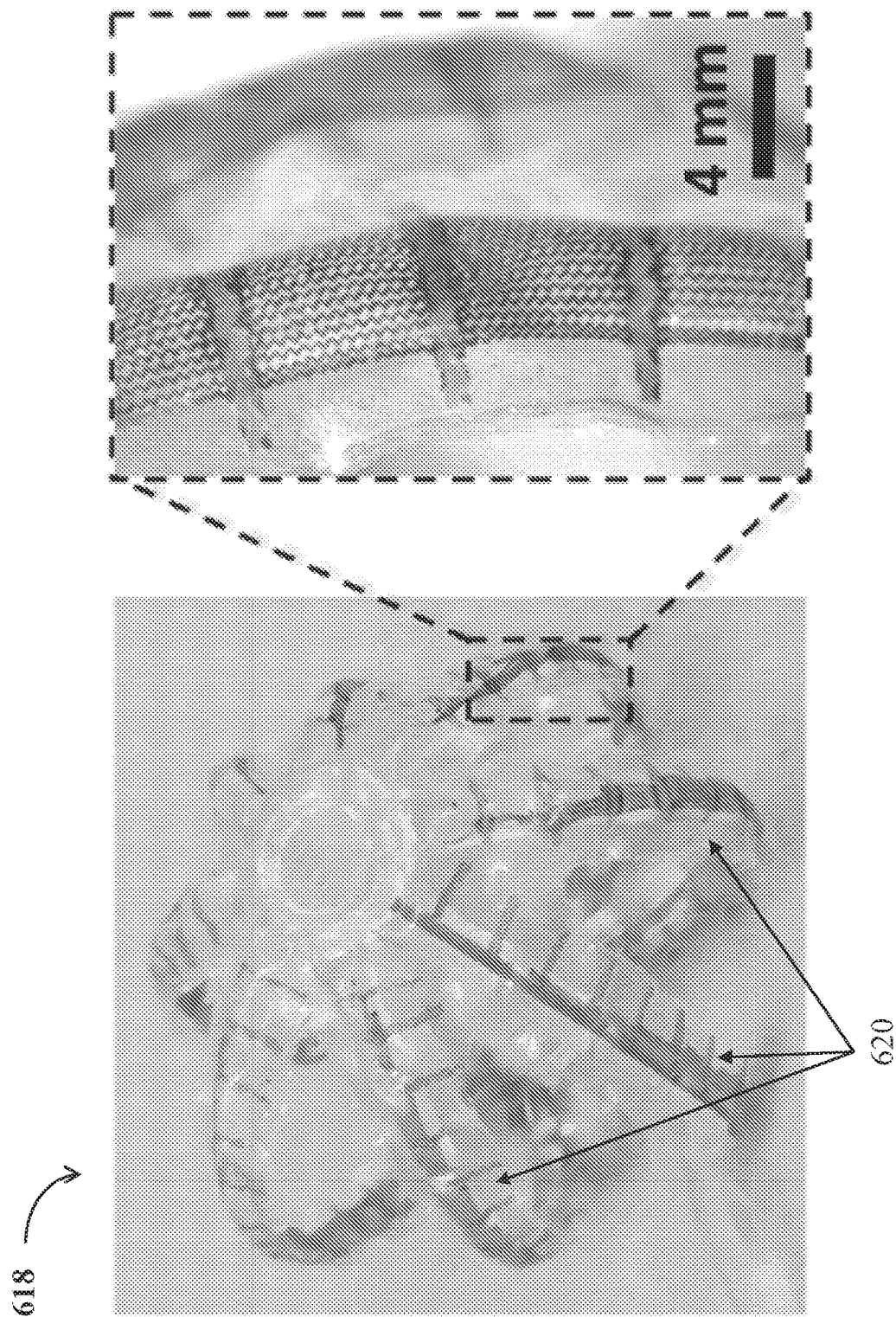

Referring now to FIG. 9G, a complex soft robotic device (or SRSA) 618 having a plurality of beams or elements 620 is shown according to example embodiments of the current disclosure. The soft robotic device (or SRSA) 618 can be fabricated by combining a plurality of the soft robotic devices 616 into a cage soft robotic (or SRSA) device. In some implementations, the soft robotic device (or SRSA) 618 can be fabricated by using a complex soft actuator having a plurality of beams or inflatable channels. The method 500 can include aligning each flexible circuit of a plurality of flexible circuits with a corresponding beam (or inflatable channel) of the plurality of beams (e.g., before inflating), and laminating each flexible circuit with a separate polymer sheet on a surface of the corresponding beam of the soft actuator. The soft robotic device 618 can be a cardiac mapping device deployable into a heart chamber using a catheter.

The method 500 allows for actuator geometries with significant complexity. It also has the benefit that because it consists of assembly of 2D planar actuator designs, these designs are intrinsically compatible with most scalable manufacturing methods for electronics. This is in contrast to many alternative methods to fabricate soft robotic actuators which require complex embedded 3D channels to allow for integration of sensors or electronics. In addition, most other actuators are intrinsically high strain to yield actuation, thus they rely on materials with greater intrinsic stretchability than conventional flex-PBCs, which limits the scalability of such designs.

According to at least one other aspect of the present disclosure, an apparatus (such as soft robotic device 616 or 618) can include an inflatable actuator and one or more flexible circuits laminated with one or more polymer sheets on a surface of the inflatable actuator. Each flexible circuit can include a plurality of insulation layer blocks 402 including a one or more circuit components 404, where each block can be connected to an adjacent block via one or more connectors 312 made from the insulation layer, and one or more electrically conductive structures 406 deposited on and defining a first surface of the one or more connectors 312, the one or more electrically conductive structures 406 can extend between and across the plurality of insulation layer blocks 402.

Figure 9H:
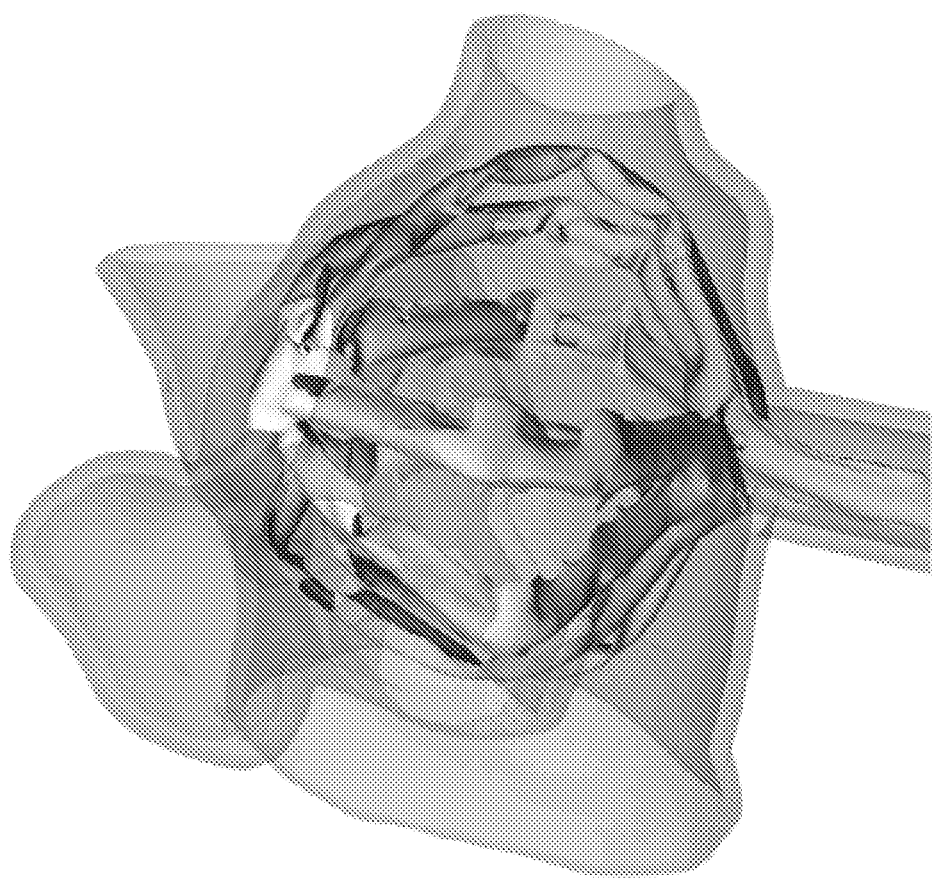

In some implementations, each connector 312 of the one or more connectors 312 can be substantially aligned with a corresponding conductive structure 314 deposited on the connector. In some implementations, the apparatus can be a cardiac mapping device deployable into a heart chamber using a catheter, as depicted in FIG. 9H. In some implementations, the inflatable actuator can include nitinol or a polymer such polyurethane.

The inflatable actuator can include a sheet of water soluble polymer 608 arranged between two layers of polymer 610. The two layers of polymer 610 can be thermally bonded around respective borders and the sheet of water soluble polymer 608 can act as a sacrificial layer to form an inflatable closed channel between the two bonded layers of polymer. In some implementations, the water soluble polymer can include polyvinyl alcohol. In some implementations, the sheet of water soluble polymer 608 can include a plurality of cutouts 614 distributed along a length of the sheet of water soluble polymer 608. The two layers of polymer 610 can be thermally bonded at the plurality of cutouts 614 to achieve bending regions 606 in the inflatable actuator 602.

In some implementations, the one or more polymer sheets can include one or more cutouts exposing portions of the one or more electrically conductive structures extending between the plurality of blocks of the insulation layer. The one or more electrically conductive structures may include copper traces deposited on the one or more connectors.

According to at least one other aspect of the present disclosure, a method for manufacturing flexible sensor arrays can include identifying one or more regions of a flexible printed circuit board (PCB) for selectively removing polymer. The flexible PCB can include one or more sensors and one or more electrically conductive serpentine structures between a first polymer layer and a second polymer layer. Each electrically conductive serpentine structure can be connected to a corresponding sensor of the one or more sensors. The method can include applying, within each region of the one or more regions, thermal energy via a heat source to a first surface of the flexible PCB along a raster path within the region such that polymer in the first polymer layer and the second polymer layer is removed from the region while a portion of the second polymer layer beneath the one or more electrically conductive serpentine structures is maintained.

Durability Analysis of Stretchable Electronics Integrated Balloons

Figure 10A:
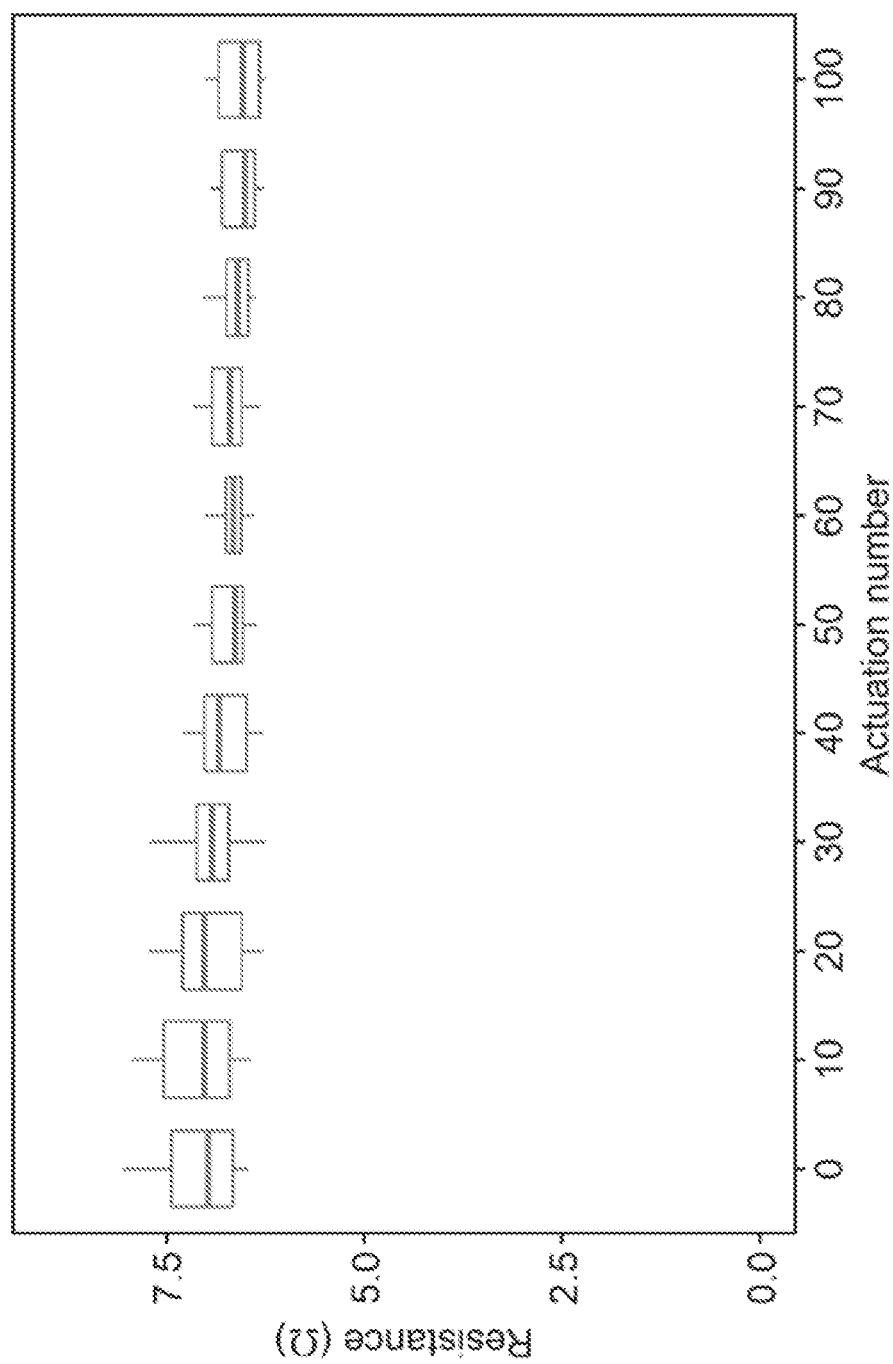
FIG. 10A-10D depict durability experimental results illustrating the durability of the soft robotic device.

Referring to FIGS. 10A-10D, two separate experiments were conducted to evaluate durability of the SRSAs or soft robotic devices, such as device 618. These results are shown in FIGS. 10A-10D. In one experiment, a single linear SRSA actuator, such as actuator 616, with a design matching that of one leg of the SRSA cage was actuated multiple times and the resulting conductivity of the individual sensor traces were subsequently assessed (using Signatone probe station, Tektronics 4200 parameter analyzer), as shown in FIG. 10A. The actuation was carried out by applying a pressure of 10 PSI which yielded a level of overall actuation consistent with those observed in the device 616 and repeated for 100 iterations in order to evaluate long term durability of the electronics under repeated loading and deformation. For each electrode, the I-V sweep was recorded, and the resistance values were plotted as shown in FIG. 10A. The values remain within the standard deviation even after 100 iterations showing excellent durability of the stretchable electronics. Resistance values for each trial is tabulated in Ohms.

Figure 10B:
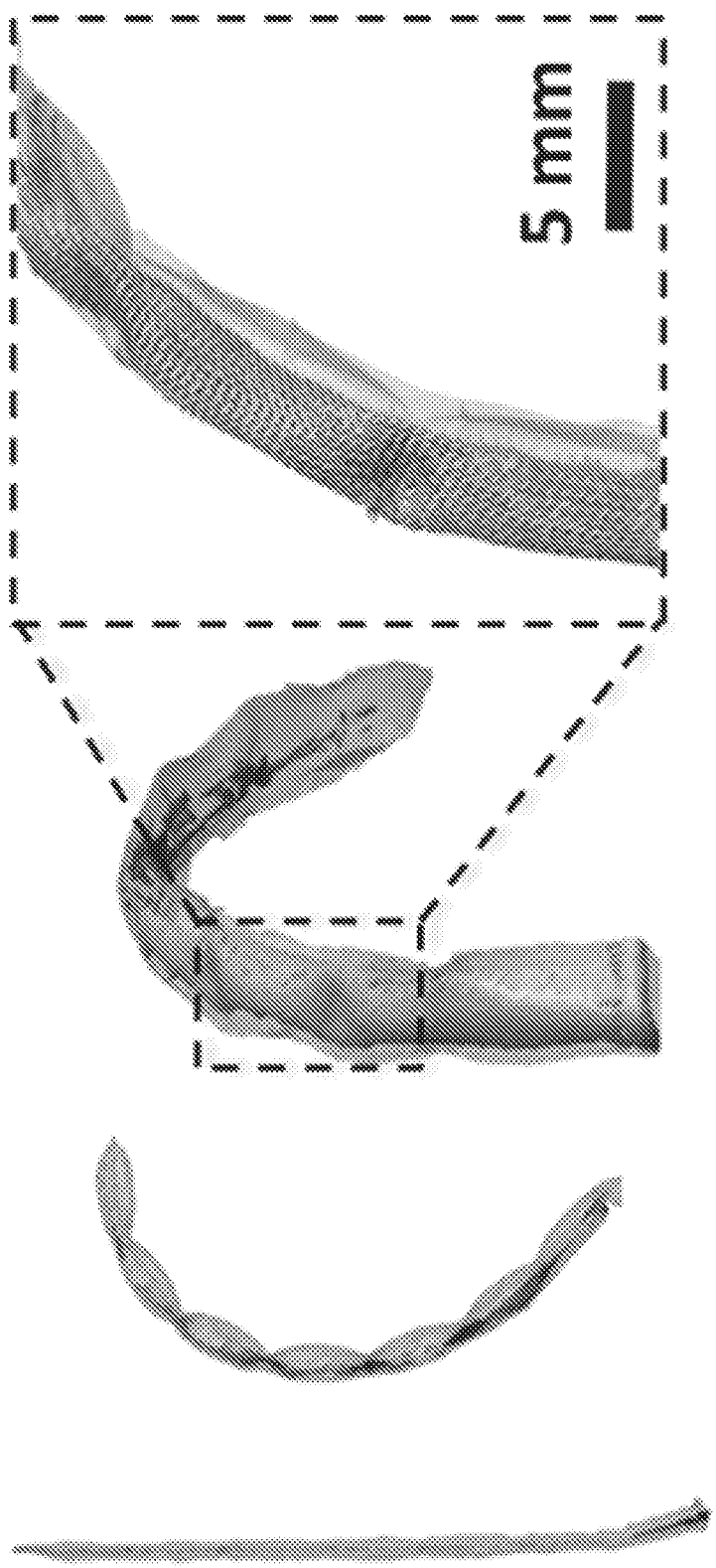

FIG. 10B shows μ-CT images and volume rendered segmentations of individual linear SRSA. The inset shows the stretchable sensor arrays on the soft robotic actuator. One reason these designs are able to demonstrate this type of durability is the low strain actuator design employed. To understand the local strain observed in the sensor arrays themselves strain in the copper traces along the length of stretchable electronics was evaluated experimentally using confocal imaging and FEA simulations (ANSYS workbench) were performed to validate these results. Note that maximum deformation occurs in pockets which are along the length of the actuator legs. The pockets (e.g., indentations 606) are part of the linear actuator design applied here, that allow for low strain actuation. They are formed by patterning the sacrificial PVA layer in a manner to allow the polymer layers to fuse in regions of the actuators such that it subsequently inflates in discrete pockets. This can be clearly observed in FIG. 10B. This pocket section is considered to measure maximum strain both in experiments and simulations.

Figure 10C:
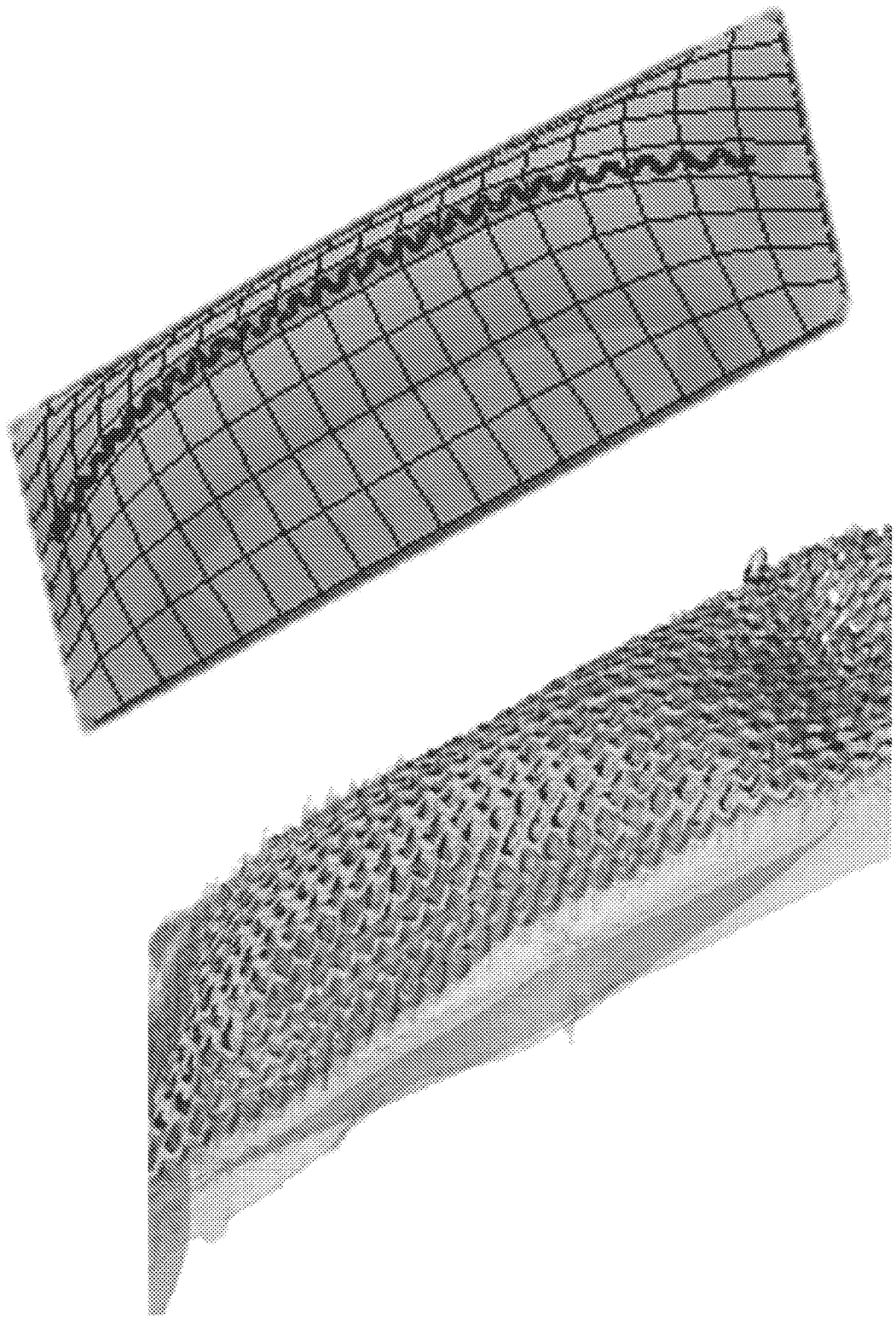
Figure 10D:
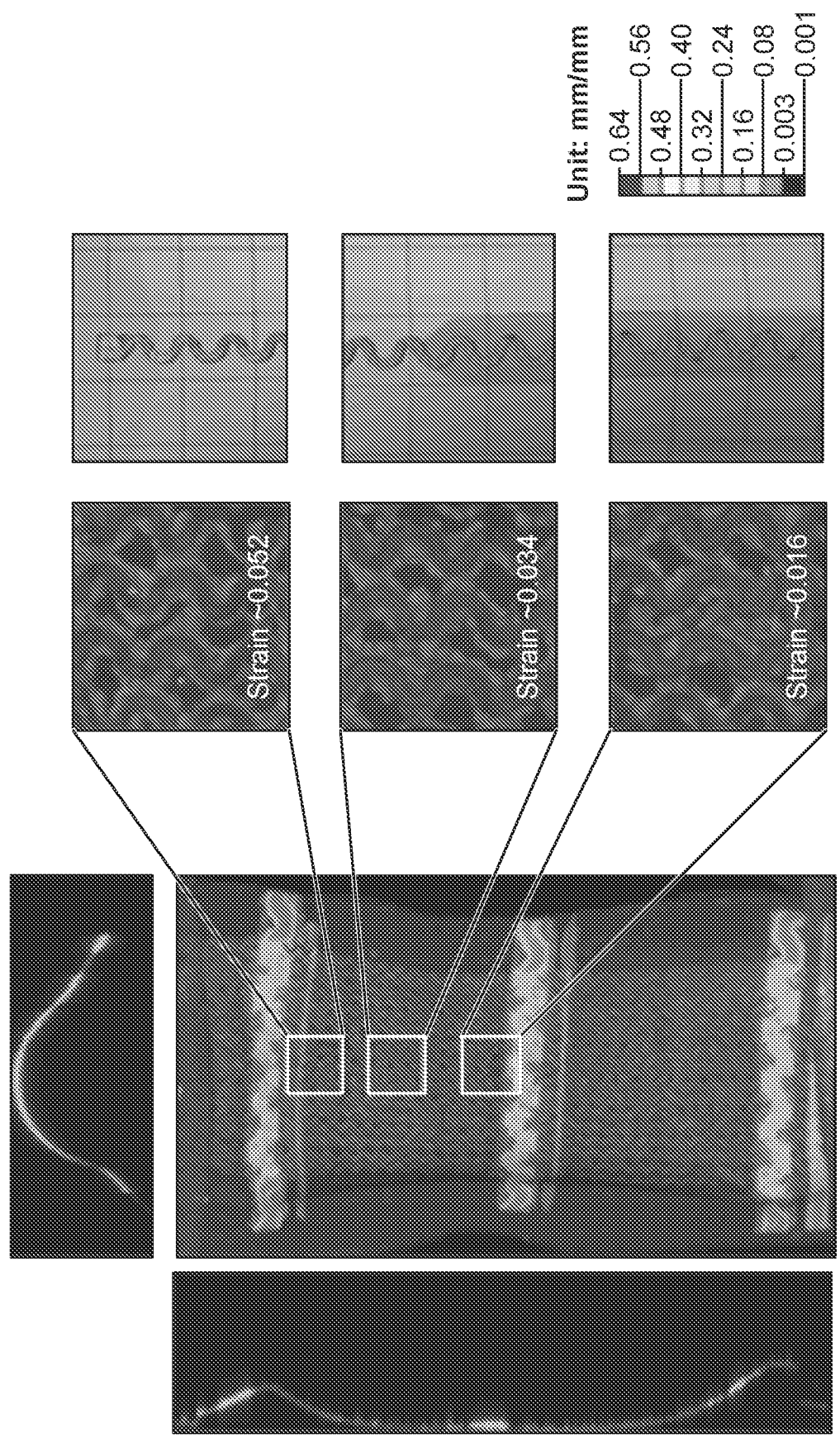

In order to evaluate the strain experimentally, confocal images of the balloon with electronics both in the non-actuated state and in actuated stated were recorded. Average strain in each section of the traces is calculated using the deformation values between the two states. FEA analysis was conducted using the static structural module of ANSYS workbench. A hyperplastic model was defined and the balloon (e.g., device 618) was actuated by applying a uniform pressure loading of 10 psi. Details of the simulation is explained further in the SI. Comparison between experimental and simulated results are shown in FIGS. 10C and 10D. The figures illustrate negligible strain along the length of the traces in the actuated state. The strain is maximum at the ends of the pocket region. We believe this is due to the constrain that is provided based on the design of these actuators. However, this maximum strain is well within the design limits for copper, thereby allowing these stretchable electronics to go through many actuation cycles. The alignment between experimental observation and simulation provides insight into the robustness and durability of these designs.

Micro CT Conformability Experiments

One goal of creating soft robotic devices or SRSAs with active soft actuators is to provide designs for sensor arrays that have the ability to conform to complex patient anatomies. In order to assess the conformability of these designs, an SRSA was deployed in four patient specific 3D printed left atria and actuated at 10 psi to obtain its final configuration within the left atrium. Volume rendered segmentations and μ-CT images (Siemens Inveon Multimodality Scanner) of deployed SRSA were used to analyze its conformability.

Figure 11:
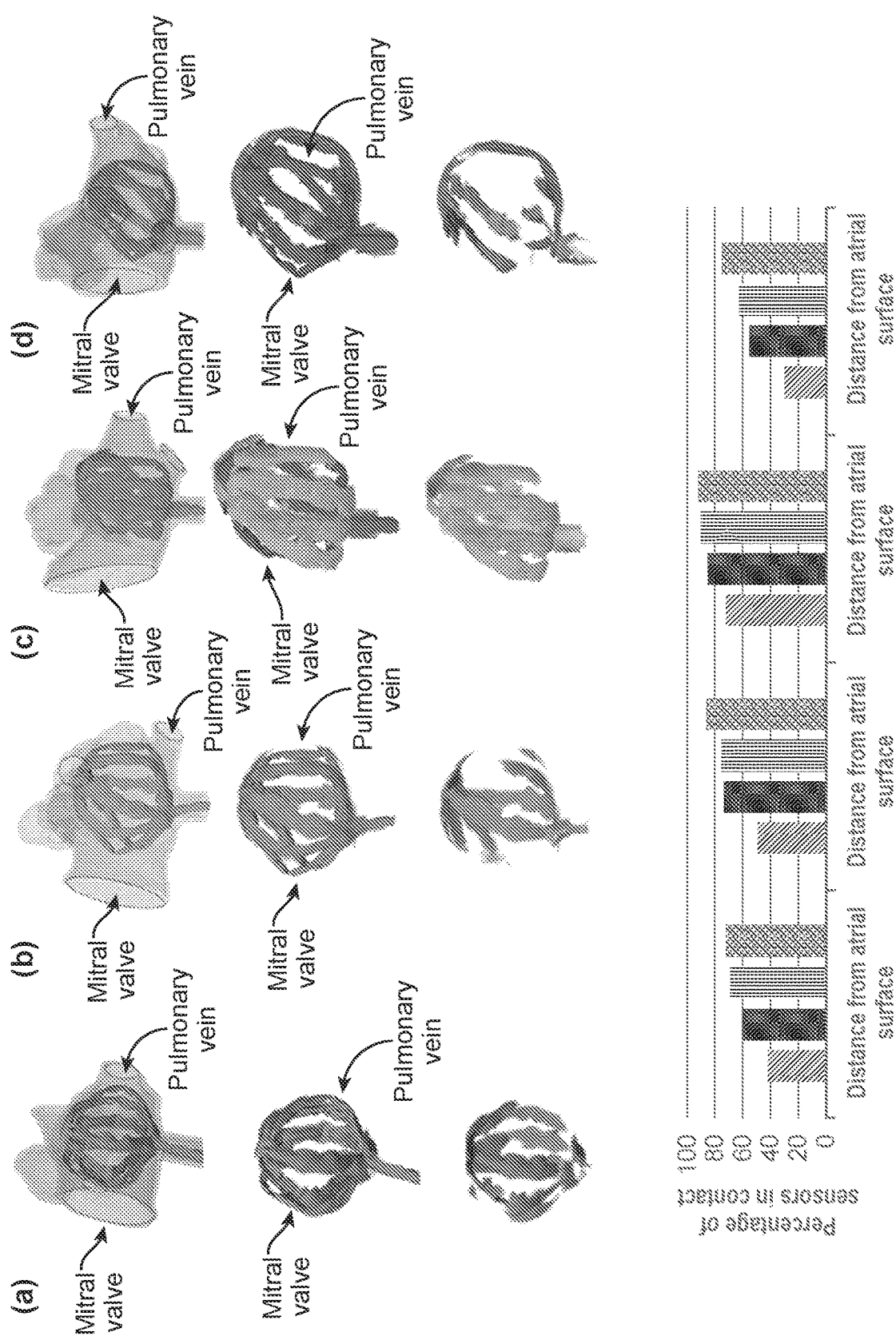
FIG. 11 depicts experimental results of Micro CT conformability experiments to assess conformability of the soft robotic device.

The results are shown in FIG. 11. The first row shows the SRSA deployed into the 3D printed atria via a mock catheter through the puncture made in the Foramen ovale in the patient's septal wall. The balloons conform to the atrial surface effectively and show no spline bunching (i.e. the individual linear actuators that form the SRSA were evenly distributed within the atria). Using mesh Boolean operations, the regions of intersections were obtained for each of these atria. Prior studies have shown that the signals can be detected by the sensors at distances greater than 2 mm from the atrial surface. Considering these values, different distances from 0 to 2 mm were color coded analogous to a thermal heat map. The heat maps are superimposed on the SRSA to show regions that are in direct contact with the atrial tissue. Graphs of proportion of sensors within a given distance from the atrial surface are plotted for each atrium. For these calculations, sensors not near tissue because they were adjacent to anatomic features such as the pulmonary veins or the left atrial appendage were ignored. SRSA shows an average conformability of ~85-90% for these randomly chosen patient specific 3D printed patient atria. Atrium 4 shows the least conformability of 75%. We believe this is associated with the buckling of SRSA that can be clearly observed from the figure. Designs that mitigate this type of buckling may represent a strategy to further increase the conformability of these devices.

In this disclosure, the development of soft robotic sensor arrays, that exhibit excellent mechanical durability and conformability when deployed within patient specific 3D printed left atria, is reported. This method employed to create these SRSAs illustrates a promising strategy for integration of soft robotics and flexible electronics for medical applications, especially those deployed via minimally invasive catheter. The mechanical durability of these devices is demonstrated by showing that sensors could undergo 100 cycles of actuation without reduction of performance. Furthermore, simulations were performed to assess the strain in electronics which showed good match with the experimental values. The SRSA was deployed using a 13.5 Fr mock catheter into patient specific soft 3D printed left atria (soft materials mimicking the atrial tissue) to analyze its conformability. SRSA shows an average conformability of ~85-90% within these atria. The current disclosure provides a novel method for scalable fabrication and integration of flexible electronics that provides a versatile approach for creating a wide variety of complex geometry actuator/sensor arrays that is broadly applicable. This enables future development of efficient devices for better treatment of AFib and cardiac arrhythmias.

While this specification contains many specific implementation details, these should not be construed as limitations on the scope of any implementations or of what may be claimed, but rather as descriptions of features specific to particular implementations of the systems and methods described herein. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

Having now described some illustrative implementations and implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementation," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. Although the examples provided herein relate to controlling the display of content of information resources, the systems and methods described herein can include applied to other environments. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

Having described certain embodiments of methods and systems, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method comprising:
   identifying one or more regions of a printed circuit board (PCB) for selectively removing insulation material, the PCB including one or more electrically conductive structures arranged on an insulation layer; and
   applying, within each region of the one or more regions, thermal energy via a heat source to a surface of the PCB within the region such that insulation material of the insulation layer is removed from the region while the one or more electrically conductive structures and a portion of the insulation layer beneath the one or more electrically conductive structures are maintained.

2. The method of claim 1, wherein applying the thermal energy includes applying the thermal energy along a raster path within the region.

3. The method of claim 1, further comprising:
   determining an output thermal energy range of the heat source to cause the insulation material of the insulation layer to be removed from the region while maintaining the portion of the insulation layer beneath the one or more electrically conductive structures; and
   setting the heat source to generate the thermal energy according to the output thermal energy range prior to applying the thermal energy to the surface of the PCB.

4. The method of claim 3, wherein the output thermal energy range is determined based on a first temperature specific to the insulation layer and a second temperature specific to the one or more electrically conductive structures.

5. The method of claim 3, wherein the output thermal energy range is based on at least one of a thickness of the insulation layer or a thickness of the one or more electrically conductive structures.

6. The method of claim 1, wherein the heat source is a laser cutter and applying the thermal energy to the surface of the PCB includes applying a laser beam of the laser cutter to the surface of the PCB according to a raster path within the region.

7. The method of claim 6, further comprising:
   determining an output power range of the laser cutter to cause the insulation material of the insulation layer to be removed while maintaining the portion of the insulation layer beneath the one or more electrically conductive structures; and
   setting the laser cutter according to the output power range prior to applying the laser beam to the surface of the PCB.

8. The method of claim 1, wherein the one or more electrically conductive structures are exposed within the one or more regions to sense electrical voltage of a surrounding environment.

9. The method of any of claim 1, wherein the one or more electrically conductive structures have a serpentine shape to allow the one or more electrically conductive structures to stretch within the one or more regions when the insulation layer is removed.

10. A method comprising:
    aligning at least one flexible circuit with a soft actuator, each flexible circuit of the at least one flexible circuit including:
      a plurality of blocks of an insulation layer including one or more circuit components, each block connected to an adjacent block via one or more connectors made from the insulation layer; and
      one or more electrically conductive structures deposited on and defining a first surface of the one or more connectors, the one or more electrically conductive structures extending between and across the plurality of blocks; and
    laminating the at least one flexible circuit with a polymer sheet on a surface of the soft actuator to form a soft robotic device, the polymer sheet configured to provide, for the at least one flexible circuit, insulation and mechanical fixation to the soft actuator.

11. The method of claim 10, wherein the soft actuator includes a plurality of beams and the method comprising:
    aligning each flexible circuit of a plurality of flexible circuits to a corresponding beam of the plurality of beams; and
    laminating each flexible circuit with a separate polymer sheet on a surface of the corresponding beam of the soft actuator.

12. The method of claim 10, wherein the soft robotic device is a cardiac mapping device deployable into a heart chamber using a catheter.

13. The method of claim 10, wherein the soft actuator includes polymer and the method further comprising manufacturing the soft actuator by:
    arranging a sheet of water soluble polymer between two layers of polymer; and
    thermally bonding the two layers of polymer around respective borders, the sheet of water soluble polymer acting as a sacrificial layer to form an inflatable closed channel between the two bonded layers of polymer.

14. The method of claim 13, further comprising:
    making a plurality of cutouts in the sheet of water soluble polymer, the plurality of cutouts distributed along a length of the sheet of water soluble polymer; and
    thermally bonding the two layers of polymer at the plurality of cutouts to achieve bending regions in the soft actuator when the soft actuator is actuated.

15. The method of claim 10, further comprising:
    making one or more cutouts in the polymer sheet, the one or more cutouts partially exposing portions of the one or more electrically conductive structures extending between the plurality of blocks of the insulation layer.

16. The method of claim 10, wherein each connector of the one or more connectors is substantially aligned with the conductive structure deposited on the connector.

17. An apparatus comprising:
    an inflatable actuator; and
    one or more flexible circuits laminated with one or more polymer sheets on a surface of the inflatable actuator, each flexible circuit including:

a plurality of blocks of an insulation layer including a one or more circuit components, each block connected to an adjacent block via one or more connectors made from the insulation layer; and one or more electrically conductive structures deposited on and defining a first surface of the one or more connectors, the one or more electrically conductive structures extending between and across the plurality of blocks.

18. The apparatus of claim 17, wherein each connector of the one or more connectors is substantially aligned with a corresponding conductive structure deposited on the connector.

19. The apparatus of claim 17, wherein the apparatus is a cardiac mapping device deployable into a heart chamber using a catheter.

20. The apparatus of claim 17, wherein the inflatable actuator includes a sheet of water soluble polymer arranged between two layers of polymer, the two layers of polymer thermally bonded around respective borders and the sheet of water soluble polymer acting as a sacrificial layer to form an inflatable closed channel between the two bonded layers of polymer.

* * * * *